US011109795B2

(12) United States Patent
Siwoff

(10) Patent No.: US 11,109,795 B2
(45) Date of Patent: Sep. 7, 2021

(54) DEVICE AND METHOD FOR MEASURING AND DISPLAYING BIOELECTRICAL FUNCTION OF THE EYES AND BRAIN

(71) Applicant: Ronald Siwoff, Chester, NJ (US)

(72) Inventor: Ronald Siwoff, Chester, NJ (US)

(*) Notice: Subject to any disclaimer, the term of this patent is extended or adjusted under 35 U.S.C. 154(b) by 399 days.

(21) Appl. No.: 16/047,935

(22) Filed: Jul. 27, 2018

(65) Prior Publication Data

US 2020/0029851 A1 Jan. 30, 2020

(51) Int. Cl.
| | | |
|---|---|---|
| *A61B 5/378* | (2021.01) |
| *A61B 5/00* | (2006.01) |
| *A61B 5/398* | (2021.01) |

(52) U.S. Cl.
CPC .......... *A61B 5/378* (2021.01); *A61B 5/398* (2021.01); *A61B 5/6814* (2013.01); *A61B 5/6821* (2013.01); *A61B 5/7285* (2013.01); *A61B 5/742* (2013.01)

(58) Field of Classification Search
CPC ....... A61B 5/378; A61B 5/398; A61B 5/6814; A61B 5/6821; A61B 5/7285; A61B 5/742; A61B 3/113; A61B 3/10; A61B 3/02; A61B 3/00
See application file for complete search history.

(56) References Cited

U.S. PATENT DOCUMENTS

| | | | | |
|---|---|---|---|---|
| 9,717,465 B2 | 8/2017 | Cox | ............................. | 600/558 |
| 2010/0283973 A1* | 11/2010 | Derr | ....................... | A61B 13/00 351/239 |
| 2014/0024964 A1* | 1/2014 | Cox | ..................... | A61B 5/6821 600/558 |
| 2014/0313488 A1* | 10/2014 | Kiderman | .............. | A61B 3/113 351/246 |

OTHER PUBLICATIONS

International Society for Clinical Electrophysiology of Vision (ISCEV) Guidelines for Clinical Visually Evoke Potentials—Update 2016 www.ISCEV.org/standards.com.

* cited by examiner

*Primary Examiner* — Patrick Fernandes
(74) *Attorney, Agent, or Firm* — Ernest D. Buff & Associates, LLC; Ernest D. Buff

(57) ABSTRACT

Apparatus, system, and computer-readable media measure electroencephalography (EEG) signals or ERG signals generated from a device that presents a series of images on a timing cycle to a subject. The apparatus comprises a Central Processing Unit (CPU), Power Supply Unit (PSU), Random Access Memory (RAM), and a hard drive (HDD). The apparatus further includes at least one electrode and a photo-sensor like a photodiode for conversion of light into electric current. The CPU is operable with software for converting the EEG or ERG signals evoked from the visual stimuli to provide data and retrieving the status of EEG signals.

27 Claims, 15 Drawing Sheets

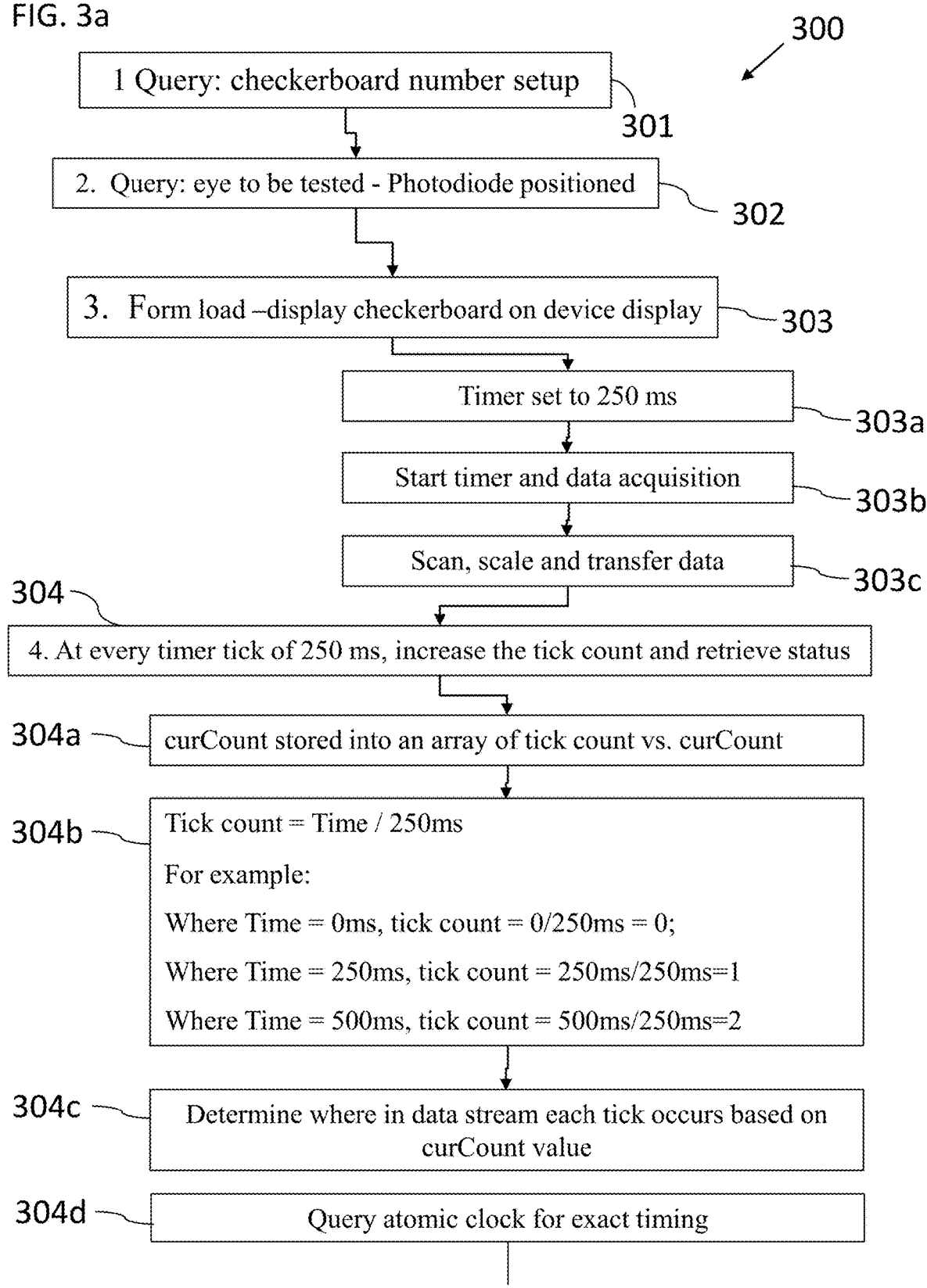

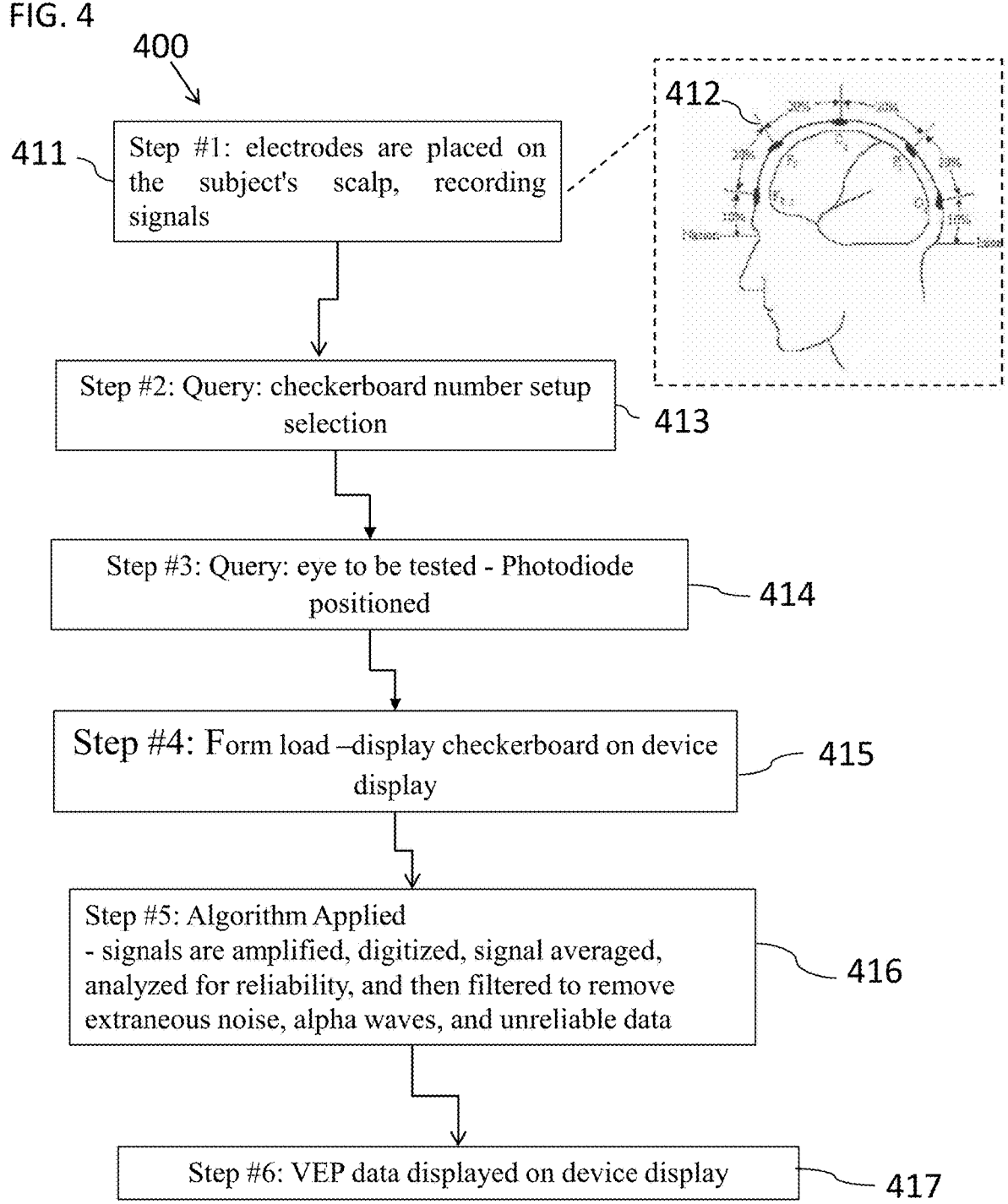

1000

1200

DEVICE AND METHOD FOR MEASURING AND DISPLAYING BIOELECTRICAL FUNCTION OF THE EYES AND BRAIN

1. FIELD OF THE INVENTION

The present invention relates to bioelectric technology used in the fields of neuro-rehabilitation, neurology, ophthalmology, and optometry; and, more particularly, to a system, apparatus, method and a computer-readable medium for extracting and processing data corresponding to electrical activity of the nervous system evoked in response to visual stimuli. The present invention further relates to both mono-focal and multi-focal applications of such systems, apparatus, method, and computer-readable medium, and to the use thereof for Visual Evoked Potential (VEP) and Electro-Retina-Gram (ERG), including Pattern Visual Evoked Potential (P-VEP) and Pattern Electro-Retinal-Gram (PERG).

2. BACKGROUND

There is a need in neuro-rehabilitation, neurology, ophthalmology, and optometry fields to accurately measure and extrapolate data to determine how the brain and eye process visual information. This data is utilized in vision testing, as well as in the diagnosis and treatment of eye disorders, diseases and cognitive disorders. Bioelectric technologies, particularly electroencephalography (EEG), are frequently utilized to determine neuro-function and/or vision examinations, including presenting a series of visual stimuli images to an observer or patient. Electrodes are placed in a position to detect electrical signals resulting from the visual stimuli, amplified, and recorded.

EEG technology can be used to measure Visual Evoked Potential (VEP). The electrodes can be placed in a position to detect electrical signals resulting from nervous activity in the brain. Typically, the electrodes are placed on the scalp.

For Electro-Retina-Gram (ERG), the electrodes are typically placed on or in vicinity to the eye, in order to measure nervous or electrical activity of the eye evoked in response to visual stimuli displayed to the eye. Contact lens electrodes or eyelid electrodes are typically used to detect the electrical signals emanating from the eye for ERG.

Generally, EEG is evoked in response to visual stimuli. VEP and ERG data are produced by presenting a visual stimulus to a subject and, at the same time, recording the data. This process is repeated several times and the data is averaged.

A variety of EEG, VEP and/or ERG devices have been provided for obtaining nervous system activity to visual stimuli. Current such devices generally use electrodes placed on or near the scalp or eye. Next the signals evoked in response to the visual stimuli are typically amplified and digitized by analog-to-digital (A/D) converter. Frequently the visual stimuli are displayed to the subject through a video display device, such as a video monitor, a video projector, or a light source. In order to manage control of the visual stimuli for repeat data points, the visual stimuli is often controlled by a computer having a central processing unit (CPU) in conjunction with a video card, hardware switch, or software switch used to rapidly switch or turn on and off the visual stimuli being displayed to the subject. This approach generally requires hardware, e.g., specialized video boards, to synchronize the evoked electrical signal data with the visual stimuli. These external hardware solutions send signals to control changes of the visual stimuli and synchronize the timing of those control signals with the evoked electrical data. The data is converted to digital data via an analog-to-digital converter and averaged, producing an averaged waveform that represents neuro-response as a function of time. During this process, evoked electrical signal data is generally processed for only a portion of the time (typically half the time) during which the patient or subject is exposed to the visual stimuli, due to the requirements to first collect and then process the data in real time. This results in a loss of efficiency and longer testing periods and may increase the incidence of asynchronous artifacts due to the subject losing concentration over time.

Attempts have been made to improve the accuracy of VEP and ERG. For example, U.S. Pat. No. 9,717,465 discloses an approach to compensate for asynchronous signals that do not correspond to display of the visual stimuli in VEP or ERG analysis. These asynchronous signals include artifacts resulting from the subject's eyes blinking. However, eliminating this asynchronous data fails to improve the sensitivity or accuracy of the equipment itself.

As a result, data developed by current VEP, ERG, and visually evoked EEG techniques is less accurate than that desired for processing of visual information.

There exists a need to further improve the accuracy of equipment and methodology useful for VEP and ERG testing. There also exists a need in the art for a device and method that processes a continuous stream of data to prevent loss of efficiency and/or data when the data stream is analyzed. Further, there is a need in the art for a device and method that synchronizes data with improved accuracy and reliability over a period of time.

SUMMARY OF THE INVENTION

The present invention provides methods, systems, and computer readable mediums operable to process a continuous stream of data and analysis by software to select a set of the data that was collected at the same time the stimulus was presented. Data can be lost due to input lags and/or output lags which result in time lags of the associated equipment.

These lags, or time drifts, have been found to result in loss of data and therefore inaccurate results in the field of VEP/ERG. Time drifts or lags (e.g., due to rise and decay time) have been found to be associated with the hardware or switches used to control signal averaging of the synchronized data and/or control of the visual display device, as well as display lags associated with the time it takes the visual display device (e.g., video monitor) to display the visual stimuli once it receives the signal. Moreover, the internal clock of every computer drifts over time, making incoming timing signals differ for each CPU device, and in turn, making clinical data less precise. Improved methods, systems and computer readable mediums can be obtained by reducing or eliminating these time drifts or lags.

Further, visually evoked electrical signals can be collected and processed in synchronized form in a continuous, non-interrupted stream, for improved efficiency and reduction of asynchronous data artifacts. The present invention can avoid fragmentation of data, preventing loss of data and avoiding inaccurate results. Data can be synchronized over a period of time, including using or calibrating to an atomic clock for accuracy.

The present invention provides a system for measuring electrical activity of a nervous system evoked from visual stimuli presented to the eye of a subject comprising:
 a. an electronic visual display device, for displaying visual stimuli to a subject;

b. at least one electrode for receiving electrical signals resulting from the subject in response to the visual stimuli;
c. an analog to digital converter that converts the signals received from the subject to digital data;
d. a digital data storage medium for recording the digital data;
e. a central processing unit (CPU) of a computer with programming to cause the display device to display the visual stimuli as a series of at least two images on a timing sequence;
f. a photosensor or sensing light emitted by the visual display device; and
g. a synchronizer, which synchronizes each of at least two consecutive images of the visual stimuli from the visual display device with the signal received by the electrode(s);

wherein the system further comprises programming to cause the CPU to calculate signal averaged digital waveforms based on an average of the signals received from at least two consecutive images of the visual stimuli.

The invention further provides a system for measuring electrical activity of a nervous system evoked from visual stimuli presented to the eye of a subject comprising:
a. an electronic visual display device, for displaying visual stimuli to a subject;
b. at least one electrode for receiving electrical signals resulting from the subject in response to the visual stimuli;
c. an analog to digital converter that converts the signals received from the subject to digital data;
d. a digital data storage medium for recording the digital data;
e. a central processing unit (CPU) of a computer with programming to cause the display device to display the visual stimuli as a series of at least two images on a timing sequence;
f. a photosensor for sensing for sensing light emitted by the visual display device; and
g. a synchronizer, which synchronizes each of at least two images of the visual stimuli from the photosensor corresponding to the beginning of the timing cycle for display of said images;

wherein the system further comprises programming to cause the CPU to calculate signal averaged digital waveforms based on an average of the signals received from at least two images of the visual stimuli.

Further provided is a method for measuring electrical activity of a nervous system evoked from visual stimuli displayed to an eye of a subject, comprising the steps of:
a. visually displaying visual stimuli to a subject as a series of at least two images with a visual display device according to a timing sequence;
b. detecting electrical signals from the subject evoked in response to the visual stimuli;
c. detecting the initial time when each of at least two consecutive images of the visual stimuli is displayed by the video display device;
d. synchronizing the evoked electrical signals with the initial time each of said images is displayed to the subject;
e. converting the electrical signals to digital data for at least two of said images; and
f. signal averaging the digital data from said images to provide a signal averaged data for the visual stimuli as a function of time.

The present invention also provides a non-transitory computer storage readable medium for a vision examination system, comprising computer-useable instructions that, when used by one or more computing devices, cause the one or more computing devices to:
a. instruct a visual display device to display visual stimuli to a subject as a series of at least two images according to a timing sequence;
b. receive electrical signals from a subject to whom said visual stimuli is displayed that evoked as a result of visual exposure to the visual stimuli;
c. receive data from a sensor for detecting the initial time when each of at least two consecutive images of the visual stimuli is displayed by the video display device;
d. synchronize the evoked electrical signals with the initial time each of said images is displayed to the subject;
e. convert the electrical signals to digital data for at least two of said images; and
f. signal average the digital data from said images to provide a signal averaged data for the visual stimuli as a function of time.

BRIEF DESCRIPTION OF THE DRAWINGS

The invention will be more fully understood and further advantages will become apparent when reference is had to the following detailed description of the preferred embodiments of the invention and the accompanying drawing, in which:

FIG. 3*a* illustrates flowchart steps 1 through 4 of an embodiment of the subject system and method;

FIG. 4 is another flow diagram showing steps of the subject method for accurately measuring and displaying VEP;

DETAILED DESCRIPTION OF THE INVENTION

Figure 1:
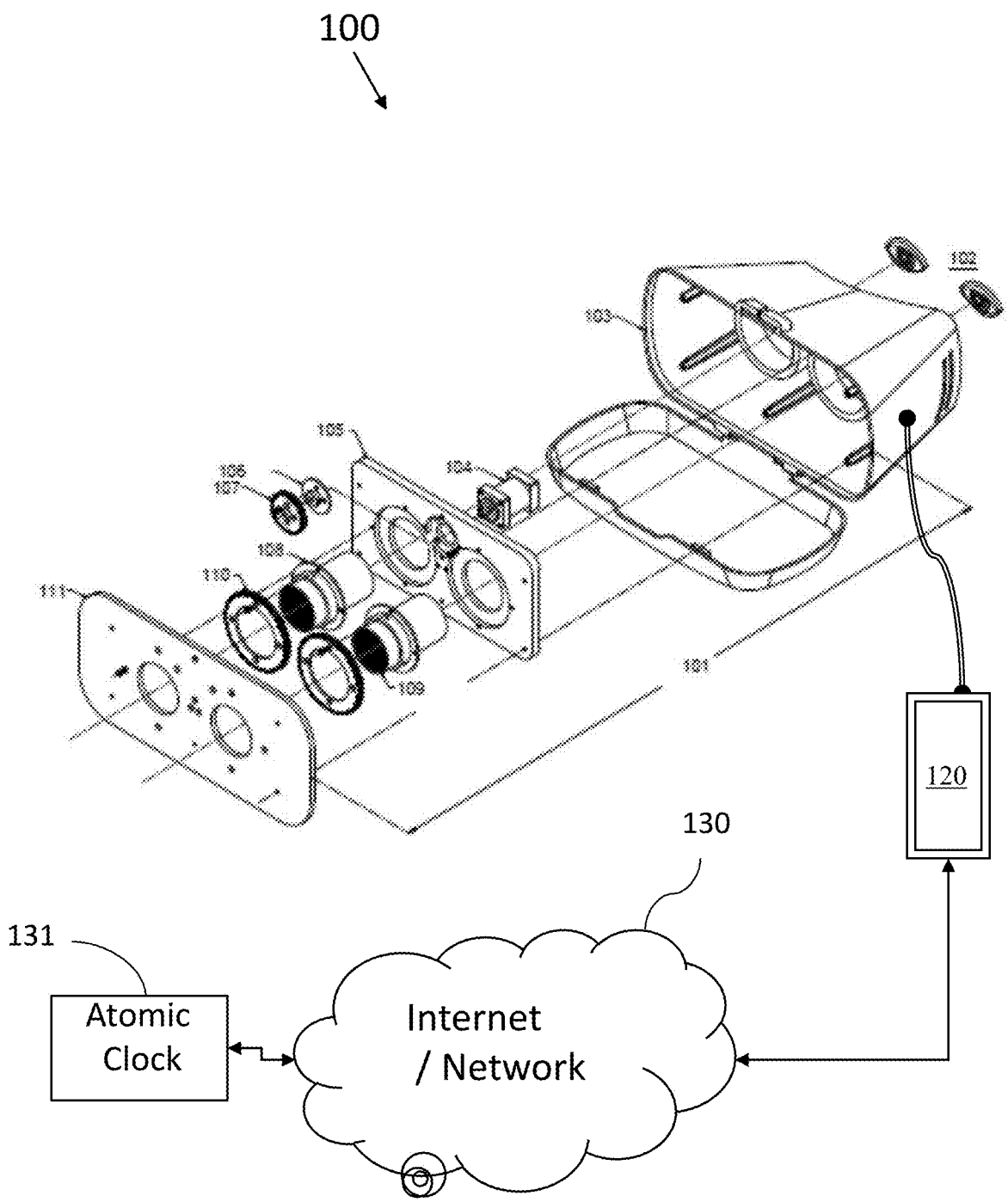
FIG. 1 illustrates a top plan view of an assembly of an embodiment of the subject invention being a High Definition Multimedia Interface (HDMI) screen, smartphone device or LCD display having a display in-line with an RS optical device headset.

Apparatus, system, and computer-readable media are described herein for measuring and displaying Visual Evoked Potential (VEP), Electro Retina-Gram (ERG), including but not limited to Pattern Visual Evoked Potential (PVEP) and Pattern Electro Retina-Gram (PERG), as well as monofocal and multifocal applications of VEP and ERG including but not limited to PVEP and PERG. In a broad aspect of the invention, there are provided means for measuring, collecting and analyzing biometric data utilizing an algorithm, photodiode and the atomic clock for displaying accurate results.

The visual stimuli include, but are not limited to, Pattern Visual Evoked Potential (P-VEP) and Pattern Electro-Retinal-Gram (PERG) data. It can be used for both mono-focal and multi-focal extraction of data, including mono-focal and multi-focal applications of ERG and VEP.

The object of the subject invention is to provide a system or method that synchronizes amplified electrical signals from the eye or brain with the presentation of stimuli generated from VEP or ERG devices for more accurate data. Synchronization can be carried out as to signals in digital or analog form—direct or indirect.

Further, the device can be connected to the Internet and include software to synchronize the computer's clock with the atomic clock or another time standard. This provides a reference standard for any computer used. Next, images are generated by the computing device using the standardized clock, which imprints a time signature to the image. Because different displays and video cards produce different rise and decay times, the current embodiment uses a photodiode, which reads the on-set and off-set of the display. This information is used for the post-processing of data streams produced by the amplifier and A/D converter. Because electro-physiological data is post-processed, more data can be collected in a shorter time, which results in more accurate VEPs and ERGs. Software post-processing corrects for the differences produced by different displays, which allows VEPs and ERGs to be conducted on cell phones, tablets, laptops, and Virtual Reality displays. The time-stamped data is adjusted for delays produced by the display. Thereafter, the time-stamped data is signal—averaged, processed, and displayed to the user in a digital format stored in a machine-readable format in both graphical and numeric format.

In accordance with the invention, an apparatus is provided for measuring electroencephalography (EEG) signals or ERG signals that presents a series of visual stimuli on a timing cycle to a subject. The apparatus can comprise a Central Processing Unit (CPU), Power Supply Unit (PSU), Random Access Memory (RAM), and a hard drive (HDD). The apparatus can further include at least one electrode and photosensor like a photodiode for conversion of light into electric current. The CPU is operable with software for (i) converting the ERG signals evoked from the visual stimuli to provide data; (ii) retrieving status of ERG signals and calculating a curCount and tick count as a function of time, wherein the tick count=Time/Time Scale; (iii) at a max tick count storing the tick count and Sample Count into a Data[x][y] array, where x=tick count and y=number of samples per image; (iv) querying an atomic clock for exact timing; (v) determining an average array based on (Data[x][y] arrays)/(total tick counts); and (vi) presenting the average array on a display with Time Scale.

The images can be presented, with a reversal rate=2 reversals per second (rps) or 1 Hz, and the Time Scale is 500 ms, preferably using ISCEV standards for pattern reversal stimulus. This is the reversal rate generally used for measuring VEP. For ERG the reversal rate is generally set to 4 reversals per second (rps) or 2 Hz, and the Time Scale is 250 ms. However other reversal rates can be used as may be desired by the operator of the equipment or method. The apparatus can comprise an amplifier that is a ready-to-use heart rate monitor front end (e.g., from a commercially available ECG equipment used for correlating ECG with heart rate) with fast restore and leads off detection features and an analog to digital converter (A/D Converter) board, wherein one analog output of the EEG or ERG device is connected to an input of the analog board and an analog input of the analog board is connected to an output of a photosensor board or the photosensor, e.g., photodiode board of a photodiode. Preferably there is a scan range for analog input set to ±2V (Input midline=1.65V), Sampling rate=1920 samples/sec (ISCEV minimum is 1000 samples/sec) Total samples=10× sampling rate (19200 samples total) for 10 seconds of scan time. Preferably the display is a monitor having an LED Backlit IPS LCD, 60 Hz refresh rate, 1920×1080 FHD, more preferably a display having 65 Hz refresh rate, 800×480 FHD, and the max tick count is equal to the number of checkerboards [20 for VEP, 40 for ERG] over a set period of time. The apparatus preferably is provided with a photodiode response time that is set at 2 µs. As such, the CPU compares a photosensitive device like a photodiode response time to produce the software timer Tick to determine an input lag and a response time delay of the display. The data is preferably extracted as a Visual Evoked Potential (VEP), electroencephalogram (EEG) measured from the scalp, Electro-Retina-Gram (ERG)(electrodes placed on the eye), Pattern Visual Evoked Potential (P-VEP) and/or Pattern Electro-Retinal-Gram (PERG) and multifocal ERG and multifocal VEP, in order to measure processing of visual information of the subject.

The present invention is directed toward a device and method for performing vision examination of the eye and brain, which includes a series of visual stimuli images presented to an observer or patient. This technology measures how the brain and eye process visual information. Such technology is useful in the field of Neuro-rehabilitation, Neurology, Ophthalmology, and Optometry; it comprises a system, method and a computer-readable medium that extracts information from a VEP or ERG, as described above. Accurate, reliable data is displayed directly and in real-time on any display, including laptops, tablets, cell phones, and virtual reality goggles.

The present invention can process a continuous stream of data, as opposed to a collection of data fragments. This continuous data stream is analyzed by software to select a set of the data that was collected at the same time the stimulus was presented.

As used herein, "visual stimuli" means any type of visual stimuli that is presented to the eye that can evoke a neurological response or electrical signal resulting directly or indirectly to the eyes ability to process it via the nervous system of the body of a subject. The visual stimuli used in the invention of the present invention can be presented as a series of two or more images presented to the subject on a timing cycle. The timing of the timing cycle is preferably consistent throughout a single evaluation, but alternatively can vary. Non-limiting examples of contemplated visual stimuli can be images of things such as but not limited to patterns, non-patterns, abstract or non-abstract designs, places, objects, faces, facial images, persons, etc. When objects are included in the visual stimuli for VEP testing, this is often referred to as Pattern VEP, or PVEP. When objects are included in the visual stimuli for ERG, this is often referred to as Patten ERG or P-ERG.

As used herein, "reversal" of an image or "reversing" an image or other visual stimulus (hereinafter referred to collectively as an "image") means changing presentation of the image, including: (1) orientation modification, including but not limited to rotated (e.g., rotated 90-180 degrees), right-side-up to upside down, mirror image; (2) light modification of the images, including but not limited to; light inversion/inverted light images (e.g., white portions turned to dark and dark portions turned to white); (3) alternating images, including but not limited to presenting in a sequence a first image, followed by a subsequent, different image; or combinations thereof; and (4) on-off, including but not limited to alternating between an "on" phase having a visual stimulus (such as but not limited to a light with a specific image or design or without a specific image or design, such as but not limited to a flash of light) and an "off" phase characterized by no or little light presented to the subject or by a reduced light cycle such as a plain grey or other color screen. Any combination of the presentation of images, or reversals thereof, can be carried out or repeated. A benefit of light modification, orientation modification, and alternating images is that photo-response data can be collected and used from both phases of the cycle, enabling twice as much data to be collected in the same period of time, or enabling more data to be obtained in the same or lesser amount of time. Preferably the following reversals of the image may be shown to the patient: orientation modification, light modification, alternating images, or combinations thereof, more preferably, orientation modification, light modification, or combinations thereof.

Luminosity of the images should remain essentially constant, except for on-off cycles, for which luminosity may be reduced during the off phase. By essentially constant is meant that the mean luminance of each image is identical with no significant change of luminance, other than minor variation during the transition between dark and light. Any significant change in luminance must be small enough to prevent a change in the evoked potential produced by the image itself. For example, a mean photopic luminance of 50 $cd/m^2$ (using a reversal rate of 2.0±0.2 reversals per second (rps) corresponds to 1.0±0.1 Hz, as a full cycle, and includes two reversals. For pattern onset/offset, a checkerboard pattern is abruptly alternated dark and light. The mean luminance of each image is identical with no significant change of luminance, other than minor variation during the transition between dark and light.

At least two images should be presented for generation of at least two data point sets, for signal averaging, preferably at least 4 sets, more preferably at least 8 sets, most preferably at least 10 sets. The upper limit can vary but for practical reasons and efficiency can be limited to 100 or less, or 50 or less, or 25 or less, or 15 or less, or 12 or less.

Different types of video display devices produce significant inter-display differences in rise and decay times. On the other hand intra-display differences for the same display do not significantly change. Standard VEP equipment cannot take advantage of improvements in video displays without a total redesign of the timing mechanism. The present software synchronization and calibration with a photodiode allow any display to be used on standard VEPs, while the internal clock on the CPU and video cards vary. That means a P100 of 98 ms on one machine may be 100.2 on another.

Video display devices useful in the present invention include, without limitation, light bulbs, LED video screens, LCD video screens, plasma video screen, cathode ray tubes (CRT) displays, including direct displays and video projects utilizing the above technologies.

In the present invention, a photo-sensor can be used to detect display of each image of the visual stimuli by the video display device. A suitable photo-sensor is a photodiode. The photo sensor recognizes any reversal and transmits a signal to the synchronizer, which can then synchronize the beginning of the presentation of the particular image of the visual stimuli with evoked neuro-response data. If a photo-electric diode is used, it can be placed on the display and is connected to the synchronizer or computer, which calibrates the display and adjusts the timing software. Using a photosensor in this manner enables a continuous stream of data to be collected and processed, whereas previously this was not the practice in VEP and ERG. It is believed that this is because it was necessary to suspend processing of the evoked electrical signal for the next successive image while the data for the previous image was processed. Without photosensor data from the visual display, prior conventional systems could not synchronize the data and process it in a continuous stream at the same time.

In the present invention, synchronization between the electrical signals evoked as a result of the visual stimuli with timing data obtained from the photo-sensor corresponding to the display of the visual stimuli images, or with the lag-adjected timing of the displayed images determined as described below, can be achieved using a synchronization algorithm.

A suitable synchronization algorithm can be: utilizing a simultaneously sampling analog-to-digital converter ("ADC"), sample both the EEG or ERG data (typically after being processed by an amplifier) and the photo-sensor. Sample the data on timing as described in more detail herein, but in any case, two or more times per cycle of the visual stimuli image timing cycle. A simultaneous ADC means that all channels are sampled at the same time. Typical EEG systems, for example, can have as few as a single channel to as many as 256 channels. For example, when sampling channels at the same time, sample 1 of the EEG/ERG amplifier directly corresponds in time to sample 1 of the photo-sensor; sample 2 of the EEG/ERG data corresponds to sample 2 of the photo-sensor, etc. This can be done for all or part (but in all cases for at least two images) of the data obtained during a particular test of the subject.

After completing test, find minimum and maximum voltage of the photo-sensor response. Calculate the numerical average of the maximum and minimum voltages. This is the "threshold" voltage. Determine the image sample numbers where the voltage passes through our threshold voltage, corresponding to when the image changes (e.g., on-of cycle, or reversals) on the video display. Average the data to provide an averaged waveform of electronic signal strength as a function of time.

This algorithm can be programmed by one of ordinary skill in the art using commercially available programming platforms, such as but not limited to C #, an object-oriented platform-independent programming language that can be implemented primarily on Microsoft Windows® operating systems. C #, as part of the .NET framework, is compiled to Microsoft Intermediate Language (MSIL). However other programming languages could also be used, such as but not limited to C++ and Java.

For any or all of the applications of the present invention, all of the sampled data can be used in the averaged waveform. Alternately, select portions of the data can be used when determining the averaged waveform. The data used in the averaged waveform can be limited to data collected in the first 150 ms, 200 ms, 250 ms, or 300 ms, preferably the first 200 ms, after each point the threshold voltage is passed, or after each change or reversal of the image is displayed.

It has been found that the present invention can provide improved accuracy and reliability of the results. Without being limited by theory, it is believed that this is due to reduction or elimination of time lag or drift, and to the ability to reduce testing time to obtain the same amount of data, and consequently reduce neurological fatigue and incidence of asynchronous data. The synchronization can also be achieved by determining lag times such as input lag associated with switches used to control the timing cycle of the visual stimuli and video display device lag associated with the time required for the video display device to present the image compared with the time it received the instruction or signal. The synchronizer then synchronizes the neuro-response data with the clock used by the CPU based on the timing that the switch, video card, or other control device sends a signal instructing the video display device to display the images, adjusting for the combined lag times. The lag times should be determined for the equipment once the equipment is warmed up and in steady state operation. Thereafter, it should be generally stable and consistent. However, if any equipment is changed or undergoes any change in operating efficiency, the lag should be recalculated or re-determined.

In the present invention, the neuro-response data also can be synchronized with the atomic clock to minimize drift of data with no difference between the present machines.

In a preferred embodiment an Internet connection and software is provided to synchronize a computer's clock with the atomic clock, thereby providing a standardized clock. This provides a reference standard for any computer used. Next, images are generated by a computing device using the standardized clock, which imprints a time signature to the image. A photo-sensor, such as a photodiode, is used to address different rise and decay times produced by different displays and video cards. The photo-sensor reads the on-set and off-set of the display. This information is used for the post-processing of the data stream produced by the amplifier and A/D converter. Because electro-physiological data is post-processed, more data can be collected in a shorter period of time; this, in turn, results in more accurate VEPs and ERGs. Software post-processing corrects for the differences produced by different displays, which allows VEPs and ERGs to be conducted on a plethora of different devices having display screens, including for non-limiting example, cell phones, tablets, laptops, computers, televisions, and/or Virtual Reality displays. The time-stamped data is adjusted for delays produced by the display and then it is signal-averaged, processed, and displayed to the user in a digital format, and stored in a machine-readable format in both graphical and numeric format.

Current International Society for Clinical Electrophysiology of Vision (ISCEV) Guidelines provides guidance regarding the measurement and definition of stimulus parameters for VEP's. See Society for Clinical Electrophysiology of Vision (ISCEV) Guidelines for clinical visually evoked potentials—2016 update, found at VEP Standard 2016 draft 2016 Feb. 24 jv012.docx02-24. The stimuli may be generated on a screen with the viewing distance, typically between 50 cm and 150 cm, adjusted to a suitable field size for any physical size of display screen. Mean photopic luminance of 50 cd/m$^2$ (with an acceptable obtained using a reversal rate of 2.0±0.2 reversals per second (rps). This corresponds to 1.0±0.1 Hz, as a full cycle, includes two reversals.

ISCEV Standard for full-field clinical electroretinography (2015 update) provides an updated and revised ISCEV Standard for full-field clinical electroretinography (ffERG or ERG). Defined ISCEV Standard ERG series includes six protocols named according to the stimulus (flash strength in cd·s·m$^{-2}$) and the state of adaptation: 1. Dark-adapted 0.01 ERG (a rod-driven response of on bipolar cells); 2. Dark-adapted 3 ERG (combined responses arising from photoreceptors and bipolar cells of both the rod and cone systems; rod dominated); 3. Dark-adapted 10 ERG (combined response with enhanced a-waves reflecting photoreceptor function); 4. Dark-adapted oscillatory potentials (responses primarily from amacrine cells); 5. Light-adapted 3 ERG (responses of the cone system; a-waves arise from cone photoreceptors and cone Off-bipolar cells; the b-wave comes from On- and Off-cone bipolar cells); and 6. Light-adapted 30 Hz flicker ERG (a sensitive cone-pathway-driven response). According to ISCEV 2015 guidelines, preparation of the patient includes: (i) Maximally dilate the pupils; (ii) Before dark adapted protocols—20 min of dark adaptation; (iii) Before light adapted protocols-10 min of light adaptation; (iv) Present low strength flashes before stronger flashes—so that the partial light adaptation due to bright light does not occur; (v) Insert corneal contact electrodes (when these are used) under dim red light after dark adaptation period. Avoid strong red light. (vi) Allow 5 min of extra dark adaptation after insertion of contact lens electrode; (vii) Allow at least 30 min recovery time in ordinary room illumination after use of strong light for retinal imaging (fundus photography, fluorescein angiography and others); and (viii) Request the patient to fix and not move eyes. Ocular movements can change the positions of electrodes, can cause blockage of light by eyelids or electrode and may induce electrical artifacts. Electrodes that contact the cornea, bulbar conjunctiva or skin on the lower eyelid are used as active electrodes connected to the positive input for recording ISCEV Standard full-field ERGs. These include contact lens electrodes, conductive fibers and foils, conjunctival wire loops, corneal wicks and skin electrodes. ISCEV Standards require full-field (Ganzfeld) stimulation be used to provide uniform luminance over the entire visual field of the test subject. This is usually achieved using a dome or integrating sphere. A fixation spot should be provided, and stimulators should allow observation of the eye to monitor fixation. Standard flash and background are defined as visibly white, with CIE coordinates near x=0.31, y=0.32. Both photopic and scotopic luminance levels are specified for each stimulus.

Under ISCEV Standards scotopic (rod) responses are isolated by dark-adaptation for a minimum of 20 minutes per ISCEV standards followed by a short wavelength stimulus as a single flash or 10 Hz flicker. Photopic (cone) responses can be obtained either before or after dark-adaptation. Since rods cannot follow a flicker stimulus greater than 20 Hz, cone photoreceptor function is primarily measured under light-adapted conditions for at least 10 minutes with either single flash (stimulus wavelength greater than 680 nm) or 30

Hz flicker stimulus. Photopic responses result in small b-wave amplitudes with a short latency (30-32 ms), whereas scotopic (rod) conditions produce much larger b-wave amplitudes with a longer latency (60 ms). Elements are stimulated in a pseudo-random sequence of light and dark, called a maximum length sequence (or m-sequence). Resulting waveforms are similar to those of the ffERG: initial negative deflection (N1 or a-wave), followed by a positive deflection (P1 or b-wave), and a second negative deflection (N2 or c-wave).

Skin electrodes such as sintered silver-silver chloride, standard silver-silver chloride, or gold cup electrodes are recommended for recording VEPs. The skin should be prepared by cleaning and a suitable paste or gel used to ensure a good, stable electrical connection. The electrode-skin contact impedances should be below 5 K Ohm as measured between 20 and 40 Hz. To reduce electrical interference, electrode-skin contact impedances should differ by no more than 1 K Ohm between electrodes. Typically, electrodes are placed on the scalp relative to bony landmarks, in proportion to the size of the head. The anterior/posterior midline measurements are based on the distance between the nasion and the inion over the vertex. The active electrode is placed on the occipital scalp over the visual cortex at Oz with the reference electrode at Fz. A separate electrode should be attached and connected to the ground. Commonly used ground electrode positions include the forehead, vertex (Cz), mastoid, earlobe (AI or A2) or linked earlobes. See Odorn et al., ISCEV standard for clinical visual evoked potentials—(2016 update), found at VEP Standard 2016 draft 2016 Feb. 24 jv012.docx02-24 jv012.docx (February 2016). The VEP subtracts the time locked data in response to the images presented which produces an ERG response. This signal, if averaged enough times will result in a signal that is produced by the image and not produced by random firing of the brain.

Electrodes used with ERG include eyelid electrodes and contact lens electrodes. Timing sequences of ERG are typically related to light adaptation capability of the eye and the intensity, spatial, chromatic, and characteristics of the stimulus. Preferably, the system permits the visual stimuli to be displayed as a series of at least 10 images and the CPU has programming to instruct the visual display device to display the visual stimuli image corresponding to at least one display rate in the range of from about 250 m-sec to about 500 m-sec per image, or from about 125 m-sec to about 250 m-sec per image. Examples of commercially available electrodes for ERG include, for nonlimiting example, low-impedance, fiber electrodes made from medical grade silver/nylon for corneal such as those sold under the tradename ERG electrode/disposable DTL PLUS ELECTRODE™, contact lenses for performing an electroretinogram, or ERG, operable by light stimulation of the retina made of a gold ring, angstroms (10-10 meter) thick, which can be placed in contact with a cornea using a viscous conductive liquid such as that sold under the tradename ERG electrode ERG-JET™. Types of recording electrodes include the Burrian-Allen Electrode, Dawson-Trick-Litzkow Electrode, ERG-Jet Electrode, Mylar Electrode, Skin Electrode, Cotton-Wick Electrode, and Hawlina-Konec Electrode.

The apparatus will generally include an analog amplifier with filters. The amplifier preferably can produce a gain of 100 and an op-amp set for a gain of 11, which results in an overall gain of 1100 v/v. With this arrangement, the apparatus will be capable of detecting signals of 2.7 mv. A suitable amplifier that can provide this level of amplification is available from Analog Devices Inc. (Norwood, Mass. USA), Model AD 8232.

VEP data can also be generated for purposes of this invention using VEP apparatus from Diopsys Inc. (Pine Brook, N.J. USA), such as Diopsys' NOVA™ VEP testing system) or Konan Medical USA (Irvine, Calif. USA), such as Konan's EvokeDx™ VEP testing system. Equipment from other suppliers and manufacturers can also be used. The subject system and method synchronizes the amplified electrical signals from the eye or brain with the presentation of stimuli. The device can be connected to the Internet and include software to synchronize the computer's clock with the atomic clock or other time standard to provide a reference standard for any computer used. Next, images are generated by the computing device using the standardized clock, which imprints a time signature to the image. Because different displays and video cards produce different rise and decay times, the current embodiment uses a photodiode, which reads the on-set and off-set of the display. This information is used for the post-processing of data streams produced by the amplifier and A/D converter. Because electro-physiological data is post-processed, more data can be collected in a shorter time, which results in more accurate VEPs. Software post-processing corrects for the differences produced by different displays, allowing VEPs to be conducted on cell phones, tablets, laptops, and Virtual Reality displays. The time-stamped data is adjusted for delays produced by the display. Thereafter, the time-stamped data is signal—averaged, processed, and displayed to the user in a digital format stored in a machine-readable format in both graphical and numeric format.

The amplifier is connected to the programmable analog/digital converter (A/D) device. A suitable A/D converter can be obtained from Measurement Computing Corporation, such as their Model 1608 FS Plus. Signal averaging and analysis is carried out by the subject system and method using software platforms.

The subject system and method provides a continuous sampling pattern VEP code and design. In compliance with the International Society for Clinical Electrophysiology of Vision (ISCEV) standards for clinical visual evoked potentials (2016), hardware utilized preferably includes: Measurement Computing USB-1608FS-PLUS-OEM Board-Only 16-Bit, 8-channel, 100 ks/s/ch Simultaneous-Sampling DAQ Device; ii) Analog Devices AD8232-EVALZ Board; Ready-to-use heart rate monitor front end with fast restore and leads off detection features. Total gain 1100 V/V, instrumentation amplifier gain=100, operational amplifier gain=11. In-amp applies gain and high-pass filtering at 7 Hz cutoff, two-pole for 40 dB per decade roll-off. Op-amp applies gain and low-pass filtering at 25 Hz cutoff, two-pole, Sallen-Key configuration. Output voltage at rest=midline voltage=3.3V/2=1.65V. Right Leg Drive On Input from gold cup electrodes, rides on top of midline voltage of 1.65V. Microchip MCP6031 Photodiode PICtail Plus Demo Board. XP Power IML0205S3V3 DC-DC Converter 5V to 3.3V Isolated Module, 600 mA output max with EFT/Surge Filter Setup Converts 5V from PC USB to 3.3V. Monitor: WLED Backlit IPS LCD, 60 Hz refresh rate, 1920×1080 FHD. Koramzi VR Glasses are implemented. Apple iPhone 6 with Duet Display app, allows mirroring and extended display of desktop to iPhone. Preferably, the display is a Stand-alone VGA or HDMI display, as well as Samsung Smartphones can also be utilized.

For example: CODE: Written in C #—Windows Forms utilizing Microsoft Visual Studio and DAQ Universal Library courtesy of Measurement Computing. Scan range for analog input set to ±2V (Input midline=1.65V) for best gain, sets accuracy to 1.31 mV. Sampling rate=1920 samples/sec (ISCEV minimum is 1000 samples/sec) Total samples=at least 10× sampling rate (19200 samples total) for 10 seconds of scan time. Pattern Stimulation: Checkerboard (16×16, 32×32, 64×64, 128×128), reversal rate=2 reversals per second (rps) or 1 Hz. In other words, each checkerboard is displayed for 500 ms. One analog input of USB-1608FS-PLUS OEM connected to output of AD8232-EVALZ. One analog input of USB-1608FS-PLUS OEM connected to output of MCP6031 Photodiode board.

FIG. 1 illustrates a top plan view of an assembly of an embodiment of the subject invention being a smartphone device having a display in-line with an RS optical device headset, shown generally at 100. RS optical device headset 101 is adapted to align with a patient's eyes, shown generally at 102, for collecting biometric vision data analyzed in accordance with the algorithm of the subject method. Headset 101 includes headset mount 103 (such as that sold under the tradename Tzumi VR Headset No. 4586). A motor assembly 104 is integrated within headset mount 103 (such as that sold under Stepper Motor 08Y102S-LW4). Gear housing 105 includes gear/motor adaptor 106 and 48 tooth drive gear 107, driven gear adaptor (2) 108, lens extension tube (2) 109, 96 tooth driven gear (2) 110, and mounting plate 111 flush mounted when assembled to yield RS optical device headset 101. RS optical device headset is configured to interact with a device having a display, herein shown generally as a smartphone shown generally at 120, implemented software downloadable for accurately measuring visual biometric data and displaying the data on the device's display. Smartphone 120 and/or headset 101 has Internet capability and is capable of connecting and communicating over the Internet by way of a carrier Network, as shown generally at 130, for communication with the atomic clock shown generally at 131 for precise time data download. Smartphone 120 includes at least one universal serial bus (USB) port, as well as wireless Network carrier, Wi-Fi and/or Bluetooth capabilities. Headset 101 preferably includes at least one USB port hardware and circuitry. Smartphone 120 may be connected to headset 101 by way of a USB. Alternatively, headset 101 includes Network carrier capability, Wi-Fi and/or Bluetooth hardware and software for wireless connectivity with of headset 101 with Smartphone 120.

Continuous Sampling Pattern VEP Code and Design Hardware Utilized via Smartphone: Measurement Computing USB-1608FS-PLUS-OEM Board-Only 16-Bit, 8-channel, 100 ks/s/ch Simultaneous-Sampling DAQ Device Analog Devices AD8232-EVALZ Board Ready-to-use heart rate monitor front end with fast restore and leads off detection features. Total gain 1100 V/V, instrumentation amplifier gain=100, operational amplifier gain=11. In-amp applies gain and high-pass filtering at 7 Hz cutoff, two-pole for 40 dB per decade roll-off. Op-amp applies gain and low-pass filtering at 25 Hz cutoff, two-pole, Sallen-Key configuration. Output voltage at rest=midline voltage=3.3V/2=1.65V. Right Leg Drive On. Input from gold cup electrodes, rides on top of midline voltage of 1.65V.j Microchip MCP6031 Photodiode PICtail Plus Demo Board. XP Power IML0205S3V3 DC-DC Converter 5V to 3.3V Isolated Module, 600 mA output max with EFT/Surge Filter Setup Converts 5V from PC USB to 3.3V. Monitor: LED Backlit IPS LCD, 60 Hz refresh rate, 1920×1080 FHD Koramzi VR Glasses. Preferably, the display is a Stand-alone VGA or HDMI display, as well as Samsung Smartphones can also be utilized CODE: Written in C #—Windows Forms utilizing Microsoft Visual Studio and DAQ Universal Library courtesy of Measurement Computing. Scan range for analog input set to ±2V (Input midline=1.65V) for best gain, sets accuracy to 1.31 mV Sampling rate=1920 samples/sec (ISCEV minimum is 1000 samples/sec) Total samples=10× sampling rate (19200 samples total) for 10 seconds of scan time Pattern Stimulation: Checkerboard (16×16, 32×32, 64×64, 128×128), reversal rate=4 reversals per second (rps) or 2 Hz. In other words, each checkerboard is displayed for 250 ms. One analog input of USB-1608FS-PLUS OEM is connected to the output of AD8232-EVALZ. One analog input of USB-1608FS-PLUS OEM is connected to the output of MCP6031 Photodiode board.

Figure 2:
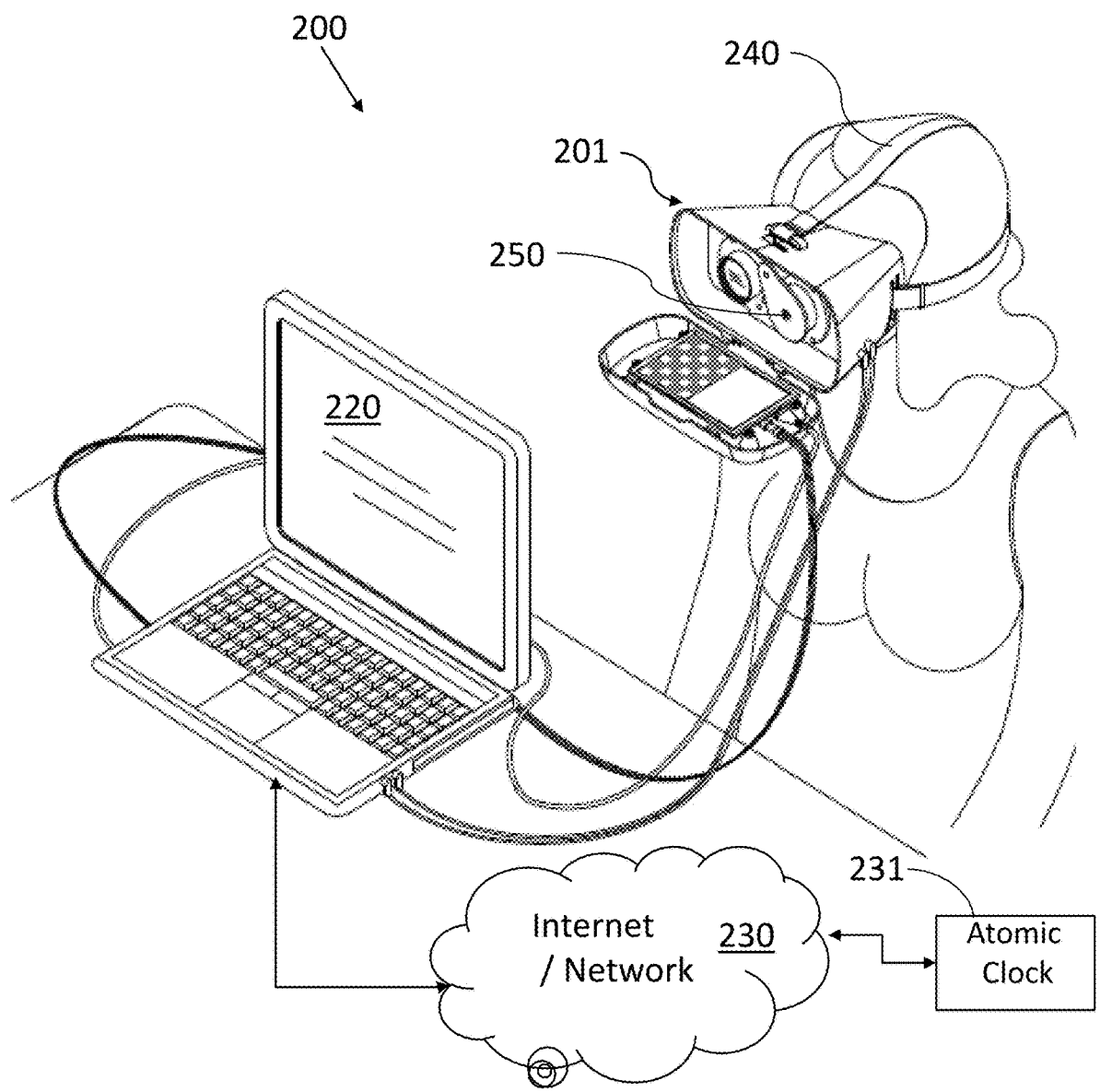
FIG. 2 illustrates a top plan view of an assembly of an embodiment of the subject invention on a laptop device having a display in-line with an RS optical device headset.

FIG. 2 illustrates a top plan view of an assembly of an embodiment of the subject invention on a laptop device having a display in-line with an RS optical device headset, shown generally at 200. An RS optical device headset 201 is adapted to align with a patient's eyes for collecting monofocal and/or multifocal biometric vision data in accordance with the invention, useful for VEP and ERG, including PVEP an PERG, analyzed in accordance with the algorithm of the subject method. RS optical device headset 201 is configured to interact with a device having a display, herein a laptop shown generally at 220. Laptop 220 includes at least one universal serial bus (USB) port, as well as a wireless Network carrier with Wi-Fi and/or Bluetooth capabilities. In turn headset 201 preferably includes at least one USB port hardware and circuitry. Laptop 220 and/or headset 101 has Internet capability and is capable of connecting and communicating over the Internet by way of a carrier Network, as shown generally at 230, for communication with the atomic clock shown generally at 231 for precise time data download. Laptop 220 is preferably connected to headset 201 by way of a USB connectivity. Alternatively, headset 201 includes Network carrier capability, Wi-Fi and/or Bluetooth hardware and software for wireless connectivity with of headset 201 with laptop 220 for real-time data acquisition and analysis. Laptop Computer (Windows 10) Measurement Computing USB-1608FS-PLUS-OEM Board-Only 16-Bit, 8-channel, 100 ks/s/ch. Simultaneous-Sampling DAQ Device. Hardware and software provided as discussed herein.

Figure 3B:
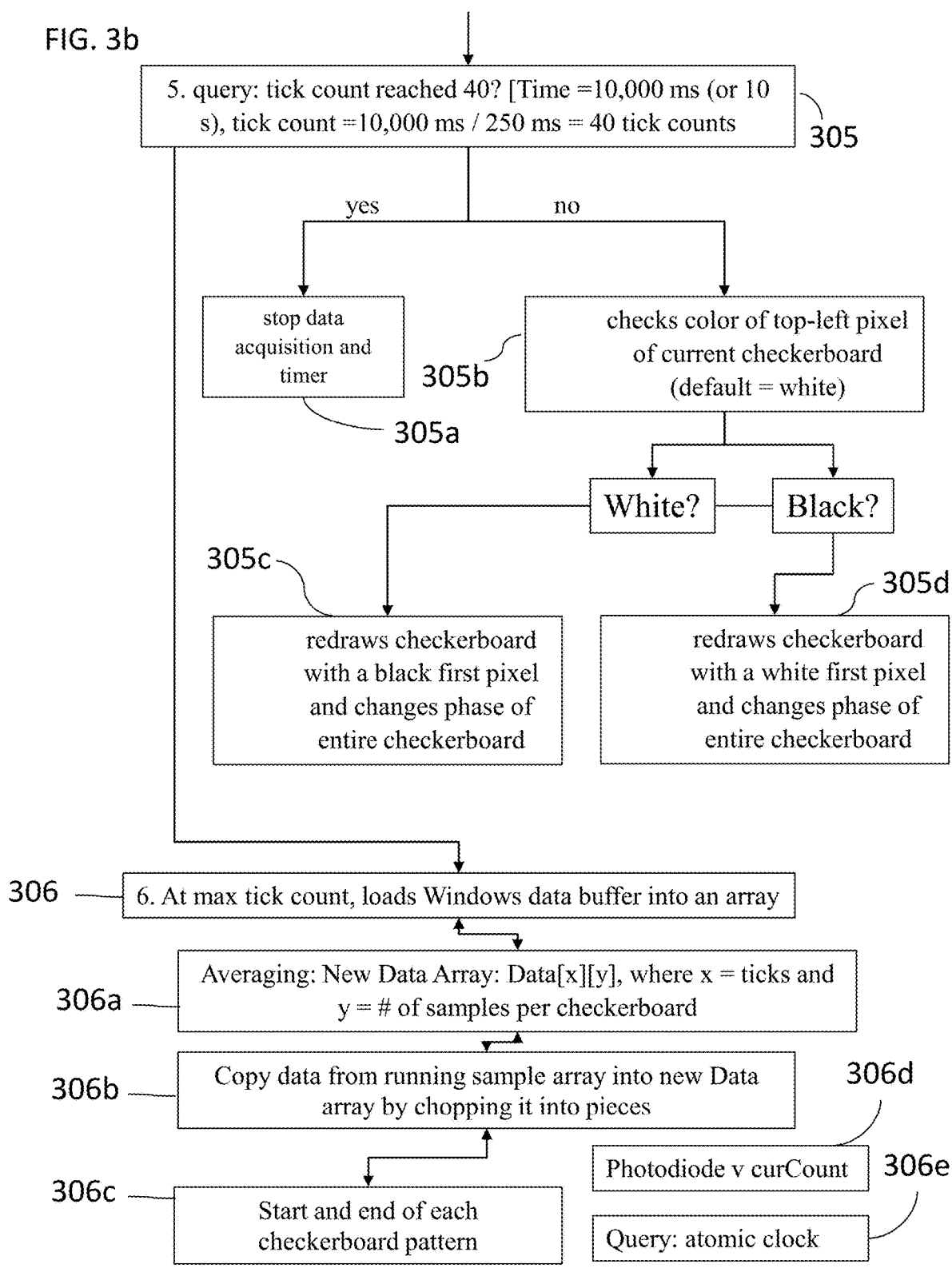
FIG. 3*b* illustrates flowchart steps 5 through 6 of an embodiment of the subject system and method.
Figure 3C:
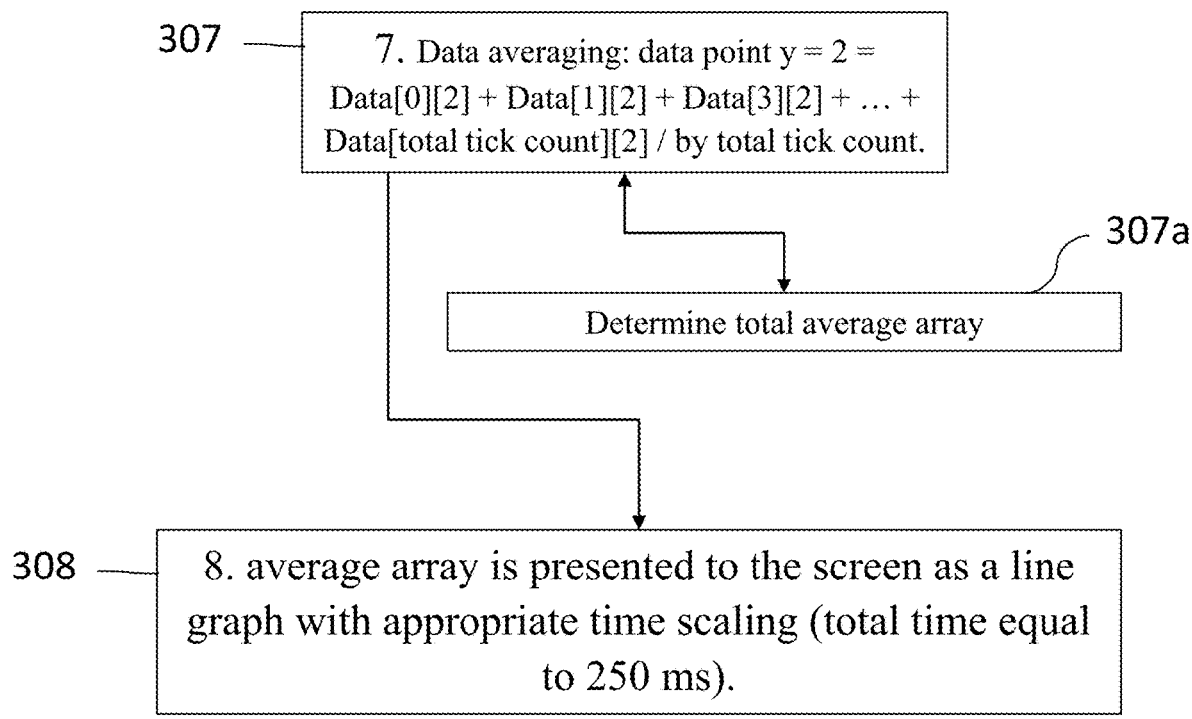
FIG. 3*c* illustrates flowchart steps 7 through 8 of an embodiment of the subject system and method.

FIGS. 3a-3c illustrate a flow chart setting forth the steps of an embodiment of the subject system and method carried out by the device, shown generally at 300. FIG. 3a illustrates steps 1 through 4; FIG. 3b illustrates steps 5 through 6; and FIG. 3c illustrates steps 7 through 8. Referring to FIG. 3a, in step 1 a message box is shown querying/asking for checkerboard setup, shown generally at 301. Valid checkerboard choices may be 16, 32, 64, and 128. These choices are provided as a non-limiting example, and may change for example with use of an HDMI display having a different display resolution. Other image types may also be used. This number is saved for use during checkerboard pattern display. Step 2, shown generally at 302, shows the message box querying as to which eye is to be tested. Valid choices are L, l, left, Left, R, r, right, Right and the checkerboard is moved to left or right side of screen accordingly. A photodiode is placed at the vertical midpoint of where checkerboard will appear. In step 3, shown generally at 303 form load is executed, loading working dimensions of the display device's screen to properly display the checkerboard on the device screen. For example, wherein the device is a smartphone, such as those sold under the tradename iPhone, the form load is executed to correspond to the working dimensions of the iPhone display screen to properly display the checkerboard on an iPhone. Next, a timer is set to 500 ms or 250 ms, as shown at 303a and Start timer and data acquisition from USB-1608FS-Plus is initiated. Scan runs in background of program and transfers data to Windows data buffer as on-board memory fills. The USB-1608FS-Plus is also capable of automatically scaling data as appropriate for input (voltage). In step 4, shown generally at 304, at every timer tick of 500 ms or 250 ms, the tick count is increased, and status of USB-1608FS-Plus is retrieved using GetStatus method provided by Universal Library. One returned value is curCount, which is the total number of samples transferred between the USB-1608FS-Plus and the Windows data buffer. This number is stored into an array of Tick Count vs. Sample Count, as shown at 304a. As shown at 304b, Tick count=Time/250 ms. For example: Where Time=0 ms, tick count=0/250 ms=0; Where Time=250 ms, tick count=250 ms/250 ms=1; Where Time=500 ms, tick count=500 ms/250 ms=2. As a result, a determination can be made as to where in the data stream each tick occurs based on curCount value, as shown at 304c. Also, the atomic clock is queried for exact timing at 304d. In step 5, shown generally at 305, the method checks/queries if the tick count has reached 40 (10 seconds/ 0.250 s=40 checkerboards over 10 seconds) [Time=10,000 ms (or 10 s), tick count=10,000 ms/250 ms=40 tick counts]. If yes, the method stops data acquisition and timer, as shown at 305a. If no, the check count has not reached 40, shown at 305b, the system checks color of top-left pixel of current checkerboard (default of first checkerboard shown is white). If white, the checkerboard is redrawn/reset with a black first pixel and the phase of entire checkerboard is changed (white to black and black to white), as shown at 305c. If black, the checkerboard is redrawn/reset with a white first pixel and changes phase of entire checkerboard (black to white and white to black), as shown at 305d.

In step 6, shown generally at 306, at max tick count, Windows data buffer is loaded into an array. At 306a, averaging is carried out, configuring a new array of arrays Data[x][y], where x is the total number of ticks (which directly correspond to number the of checkerboards) and y is the number of samples per checkerboard. At 306b, the data is copied from running sample array into a new Data array by chopping it into pieces. For example: Data[0][y] corresponds to all the data collected during the first checkerboard [x=0 ticks; y=#samples/first checkerboard]; Data[1][y] to all the data collected during the second checkerboard [x=1 ticks (time=250 ms); y=#samples/first checkerboard]; . . . Data [1+n . . . ][y for checkerboard 1+n . . . ], etc. At 306c, the start and end of each checkerboard pattern is determined/found by scanning through the data array of photodiode input. Photodiode response time is preferably set at 2 μs. Sampling of analog inputs is done simultaneously. Due to simultaneously sampling of analog inputs (on USB-1608FS-PLUS) and implementation of a fast photodiode response time of 2 μs, one can simply scan for where in time the absolute difference between two points in the photodiode data array is higher than a threshold value, adjusted for brightness of screen being tested. Black checks correspond to a low voltage (LCD blocking backlight LED), while white checks correspond to a high voltage (LCD moved to allow backlight LED to shine through). In this way, biometric data, such as VEP, ERG, P-VEP and PERG data, directly coincides with pattern display. Photodiode response is preferably compared to curCount at timer ticks to determine the input lag and response time delay of the monitor or other device being used to display the checkerboard pattern, shown generally at 306d. Preferably, the time is also compared to atomic clock queries to further ensure exact timing, shown generally at 306e.

Data averaging is executed by implementing a nested for loop that averages across all checkerboards, shown generally in step 7 at 307. Average data point=Data[x][y]/total tick count. So average of data point y=2 is accomplished by adding: Data[0][2]+Data[1][2]+Data[3][2]+ . . . +Data[total tick count][2] and dividing the sum by the total tick count. This average is then added into another array and divided by the total number of arrays to determine the total average array, shown generally at 307a.

Finally, at step 8 shown generally at 308, the average array is presented to the screen as a line graph with appropriate time scaling (total time equal to 500 ms or 250 ms). Voltage scaling is preferably already provided by the data acquisition board, but must subtract midline voltage of the AD8232 board for accurate voltage.

FIG. 4 is another flow diagram showing steps of the subject method for accurately measuring and displaying VEP, shown generally at 400. In Step #1, shown at 411, electrodes are placed on the subject's scalp for recording signals as indicated for at 412 for example representation. In Step #2, shown at 413 the method queries checkerboard number setup selection, valid choices are 16, 32, 64, and 128. This number is saved for use during checkerboard pattern display. In Step #3, shown generally at 414, the method queries as to which eye is to be tested. Valid choices are L, l, left, Left, R, r, right, Right and the checkerboard is moved to left or right side of screen accordingly. A photodiode is placed at the top-left corner of where checkerboard will appear. In Step #4, shown generally at 415 form load is executed, loading working dimensions of the display device's screen to properly display the checkerboard on the device screen. For example, wherein the device is a smartphone, such as those sold under the tradename iPhone, the form load is executed to correspond to the working dimensions of the iPhone display screen to properly display the checkerboard on iPhone. In broad Step #5, the algorithm of the method is employed, shown generally at 416, as discussed regarding FIGS. 3a-3c. A timer is set to 250 ms or 500 ms, as shown at 303a and Start timer and data acquisition from USB-1608FS-Plus is initiated. Scan runs in background of program and transfers data to Windows data buffer as onboard memory fills. The USB-1608FS-Plus is also capable of automatically scaling data as appropriate for input (voltage). Tick count, time, checkerboard, number of samples, array and curCount are determined through implementation of the algorithm of the method discussed in FIGS. 3a-3c. In Step #6, shown at 417, VEP data displayed on the device display.

Figure 5:
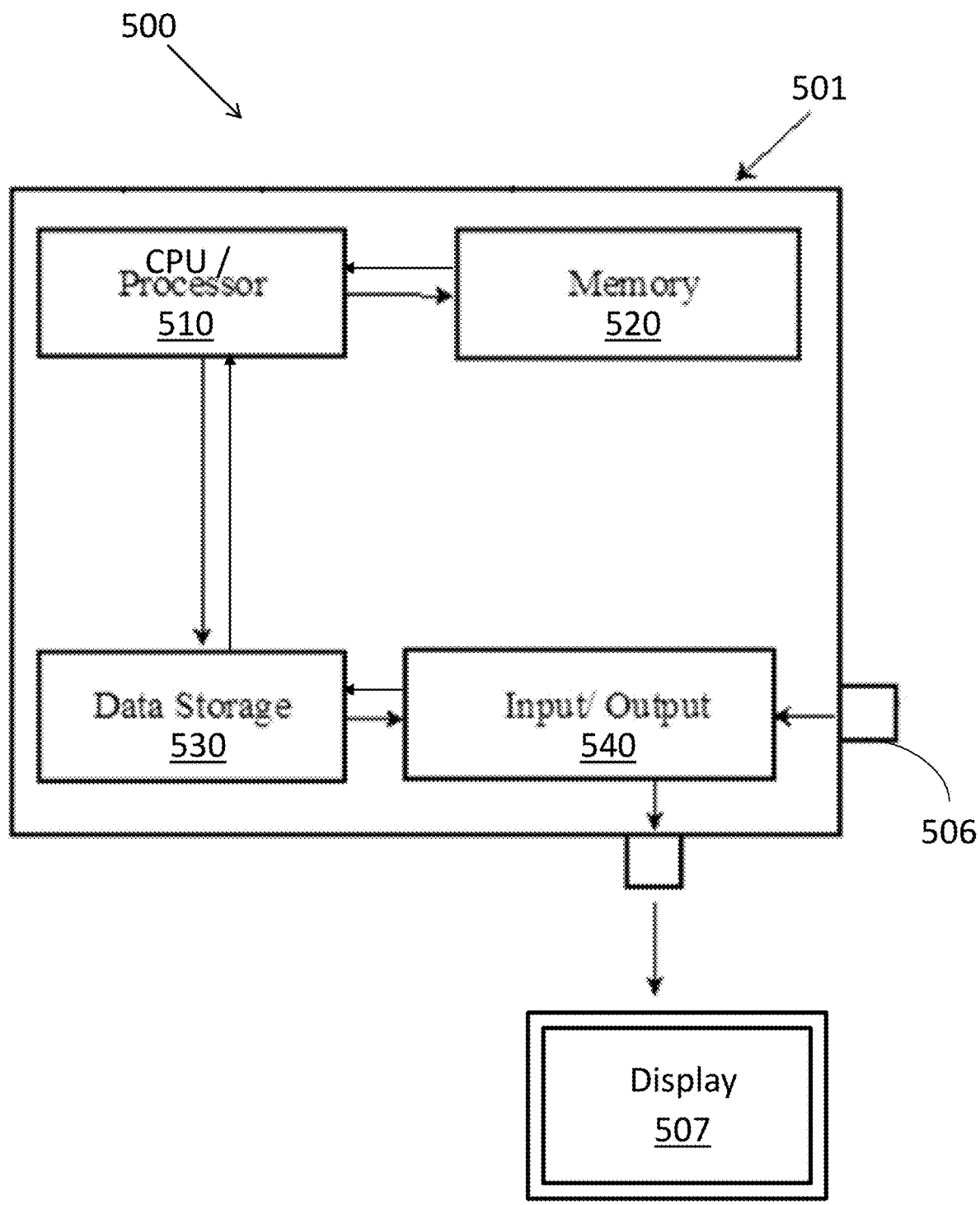
FIG. 5 is an architecture diagram depicting representative elements of a device having a display that is operable in accordance with the present invention.

FIG. 5 is an architecture diagram of representative elements of a device, shown generally at 500, having a display operable with the subject invention. Device 501 is shown as a source device or apparatus for implementation of the subject invention. Generally, the device 501 includes hardware generally configured having a module including a CPU/processor 510, a memory 520, a storage device 530, and an input/output device 540. Each of these components can, for example, be interconnected using a system bus. The processor 510 can be capable of processing instructions for execution of the subject method, system and computer-readable media within the hardware configuration. Device 501 includes a display 507 and network connection to a service provider 506.

Figure 6:
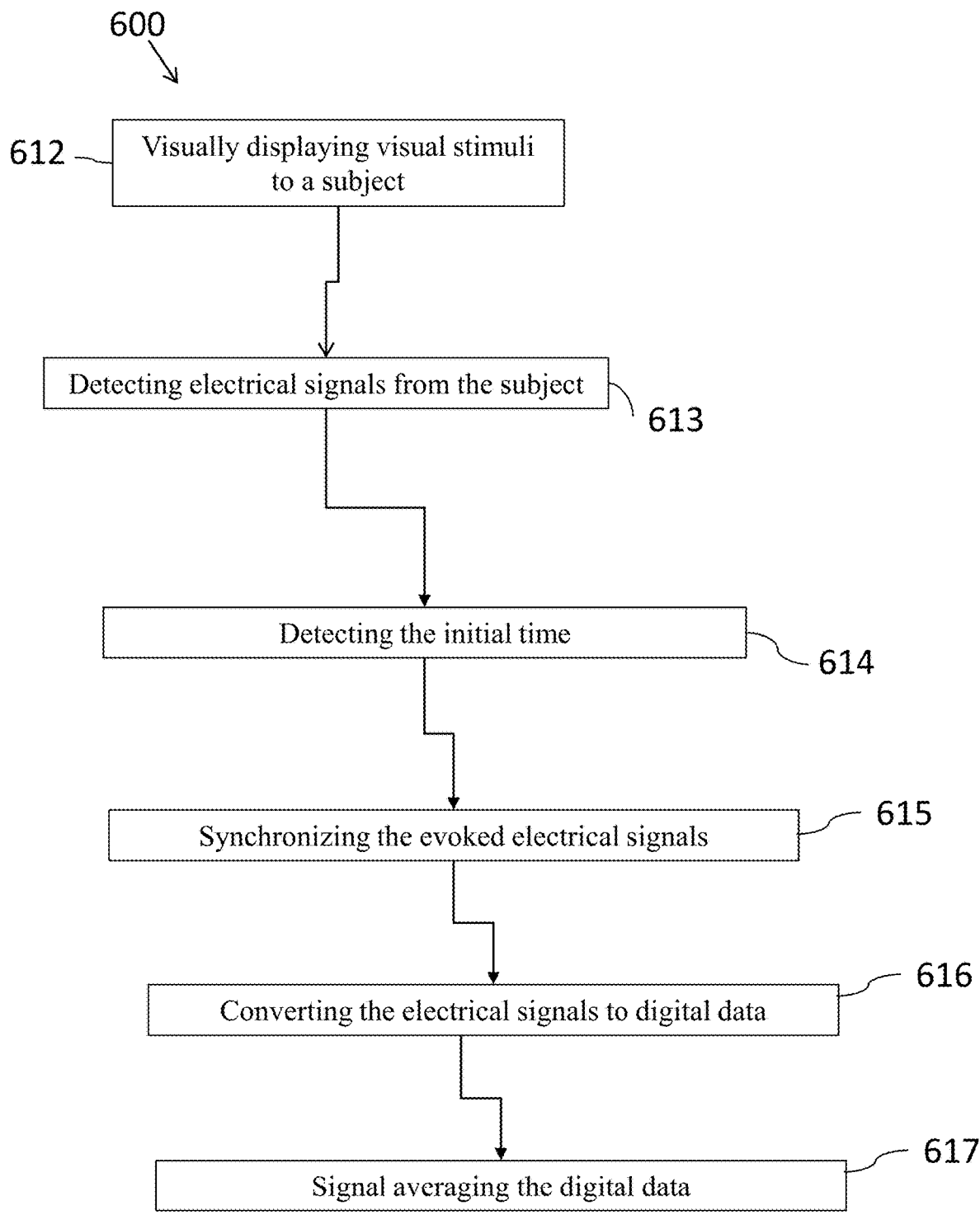
FIG. 6 is a flow diagram showing an embodiment of a method for measuring the electrical activity of a nervous system evoked from visual stimuli displayed to an eye of a subject.

FIG. 6 is flow diagram showing an embodiment of a method for measuring electrical activity of a nervous system evoked from visual stimuli displayed to an eye of a subject, shown generally at 600. The method includes the steps of: 1) at 612, visually displaying visual stimuli to a subject as a series of at least two images with a visual display device according to a timing sequence; 2) at 613, detecting electrical signals from the subject evoked in response to the visual stimuli; 3) at 614, detecting the initial time when each of at least two consecutive images of the visual stimuli is displayed by the video display device; 4) at 615, synchronizing the evoked electrical signals with the initial time each of said images is displayed to the subject; 5) at 616, converting the electrical signals to digital data for at least two of said images; and 6) at 617, signal averaging the digital data from said images to provide a signal averaged data for the visual stimuli as a function of time.

Figure 7:
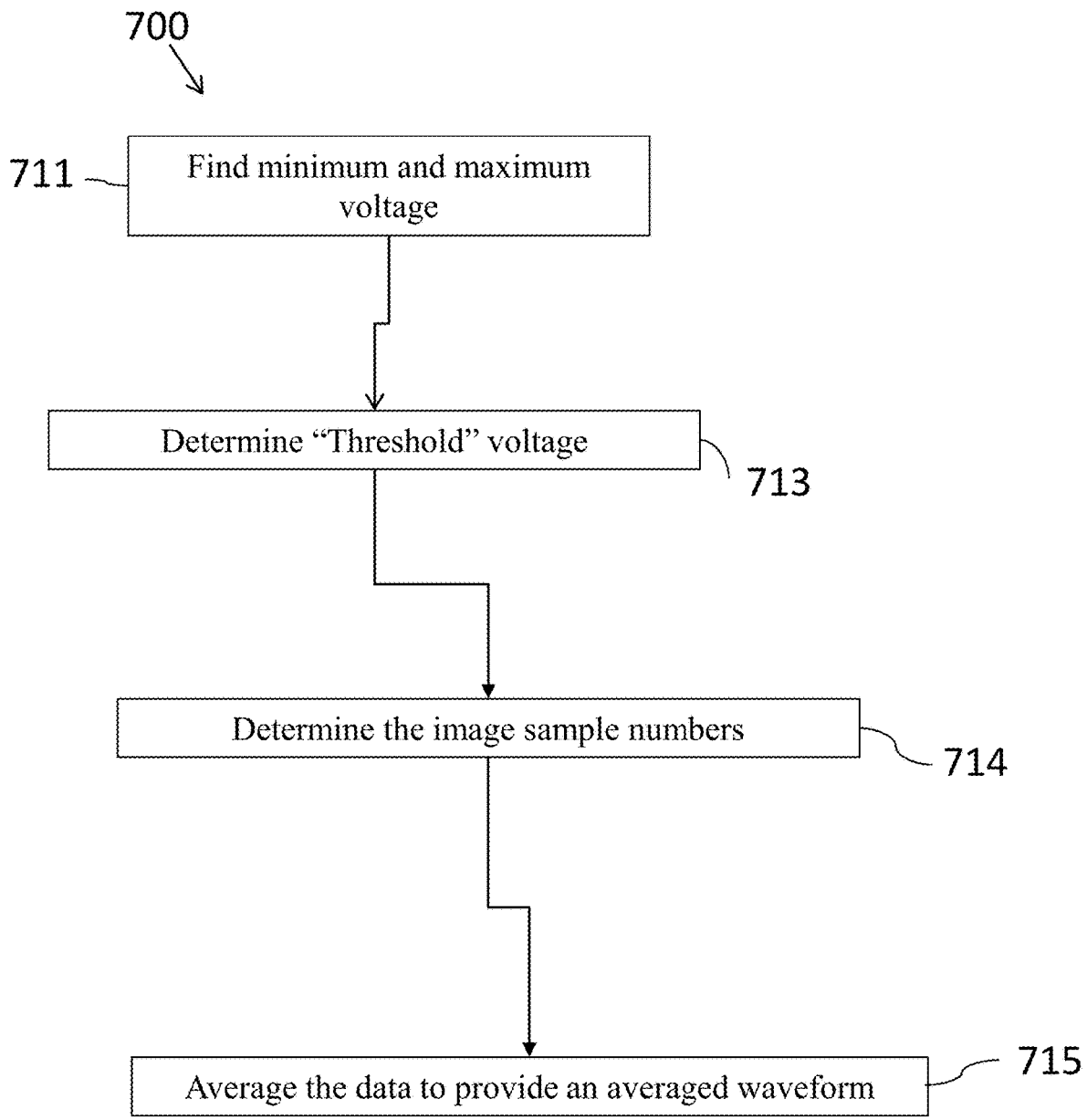
FIG. 7 is a flow diagram showing steps of an embodiment of the subject method.

FIG. 7 is flow diagram showing steps of an embodiment of the subject method, shown generally at 700. Utilizing a simultaneously sampling analog-to-digital converter ("ADC"), both the EEG or ERG data (typically after being processed by an amplifier) is sampled. Sampling of the data should be done on timing as described in more detail herein, but in any case, should be done two or more times per cycle of the visual stimuli image is displayed. At 711, after completing the test, minimum and maximum voltage of the photo-sensor response is found. At 713, the numerical average of the maximum and minimum voltages is calculated to determine the "threshold" voltage. Next, at 714, the image sample numbers where the voltage passes through our threshold voltage is determined, corresponding to when the image changes (e.g., on-of cycle, or reversals) on the video display. At 715, the data is averaged to provide an averaged waveform of electronic signal strength as a function of time.

Figure 8:
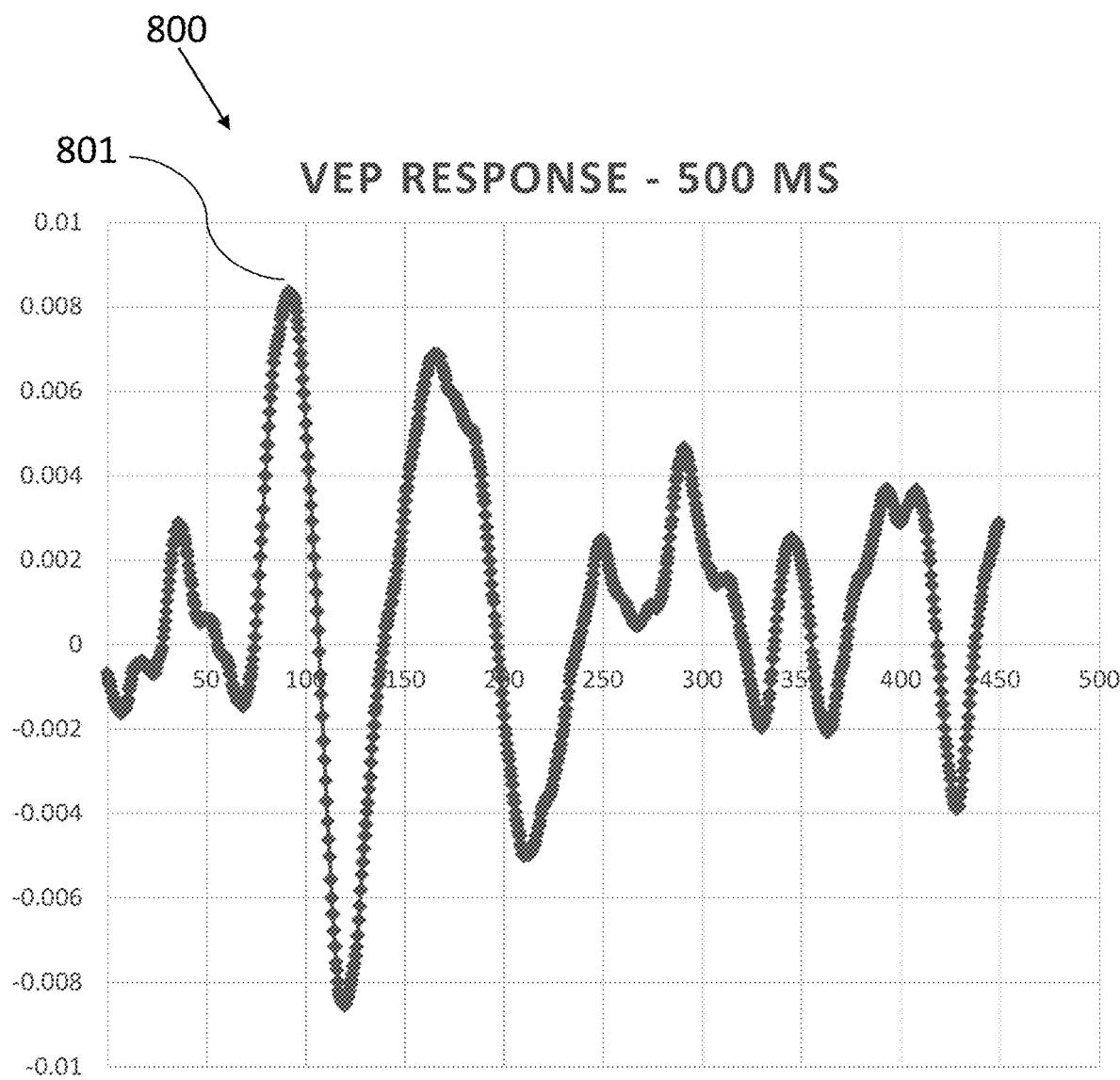
FIG. 8 is graph of an example of a VEP response at 500 ms using the subject system and method.

FIG. 8 is graph of an example of a VEP response at 500 ms using the subject system and method, shown generally at 800. At 0.008 voltages, shown at 801, the graph point indicates a primary to occipital signal arriving through eye at time ~98 ms.

Figure 9:
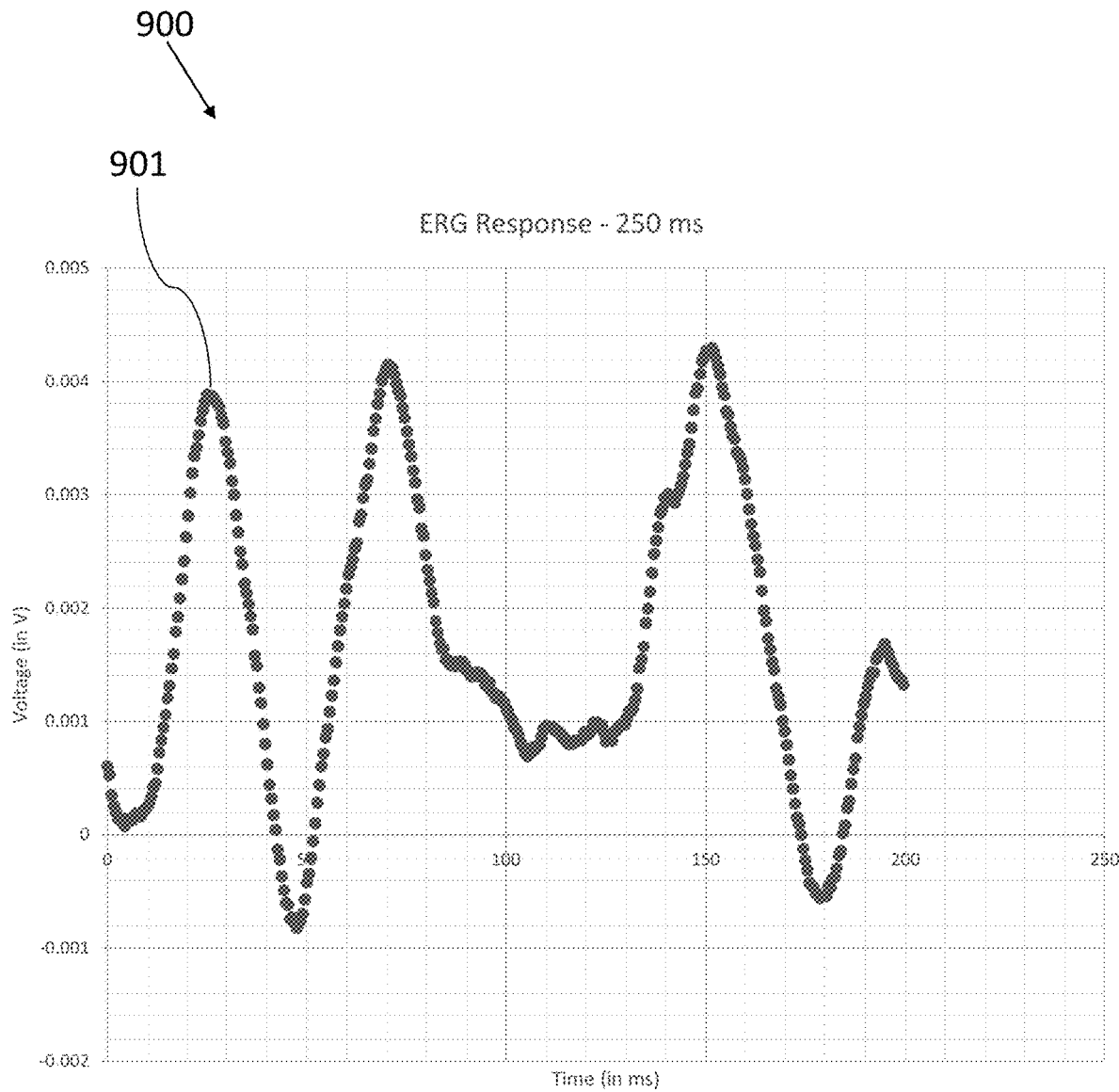
FIG. 9 is graph of an example of an ERG response at 250 ms using the subject system and method.

FIG. 9 is graph of an example of an ERG response at 250 ms using the subject system and method, shown generally at 900. At 0.0039 voltages, shown at 901, the graph point indicates a primary to occipital signal arriving through eye at a of time 25 ms (deviation: +/−2 ms).

Figure 10:
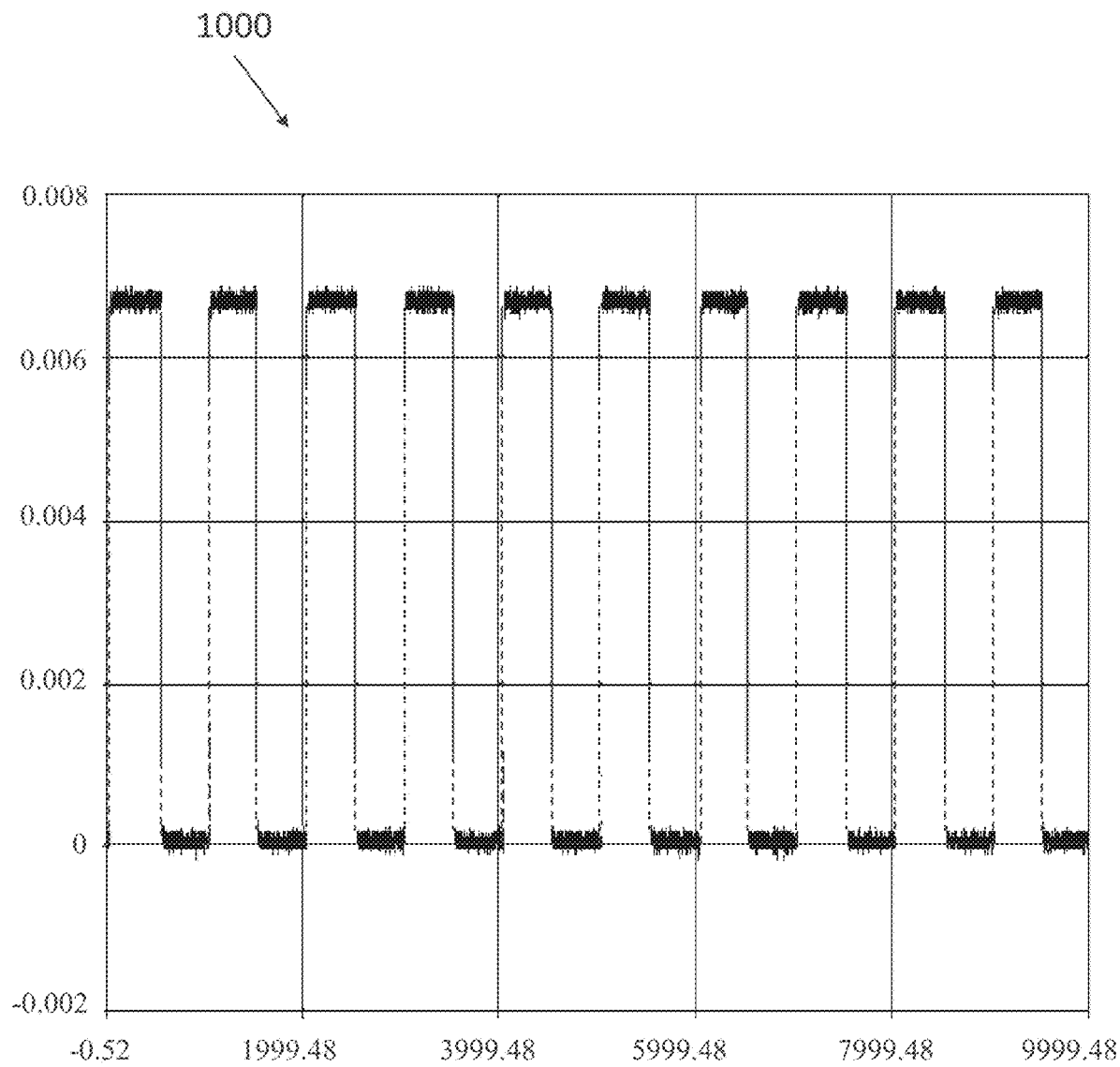
FIG. 10 is graph of an example of a VEP showing photo response at 10 seconds, 1 Hz (2 reversals/second), start points 85%-15%, using the subject system and method.

FIG. 10 is graph of an example of a VEP showing photo response at 10 seconds, 1 Hz (2 reversals/second), start points 85%-15%, using the subject system and method, shown generally at 1000.

Figure 11:
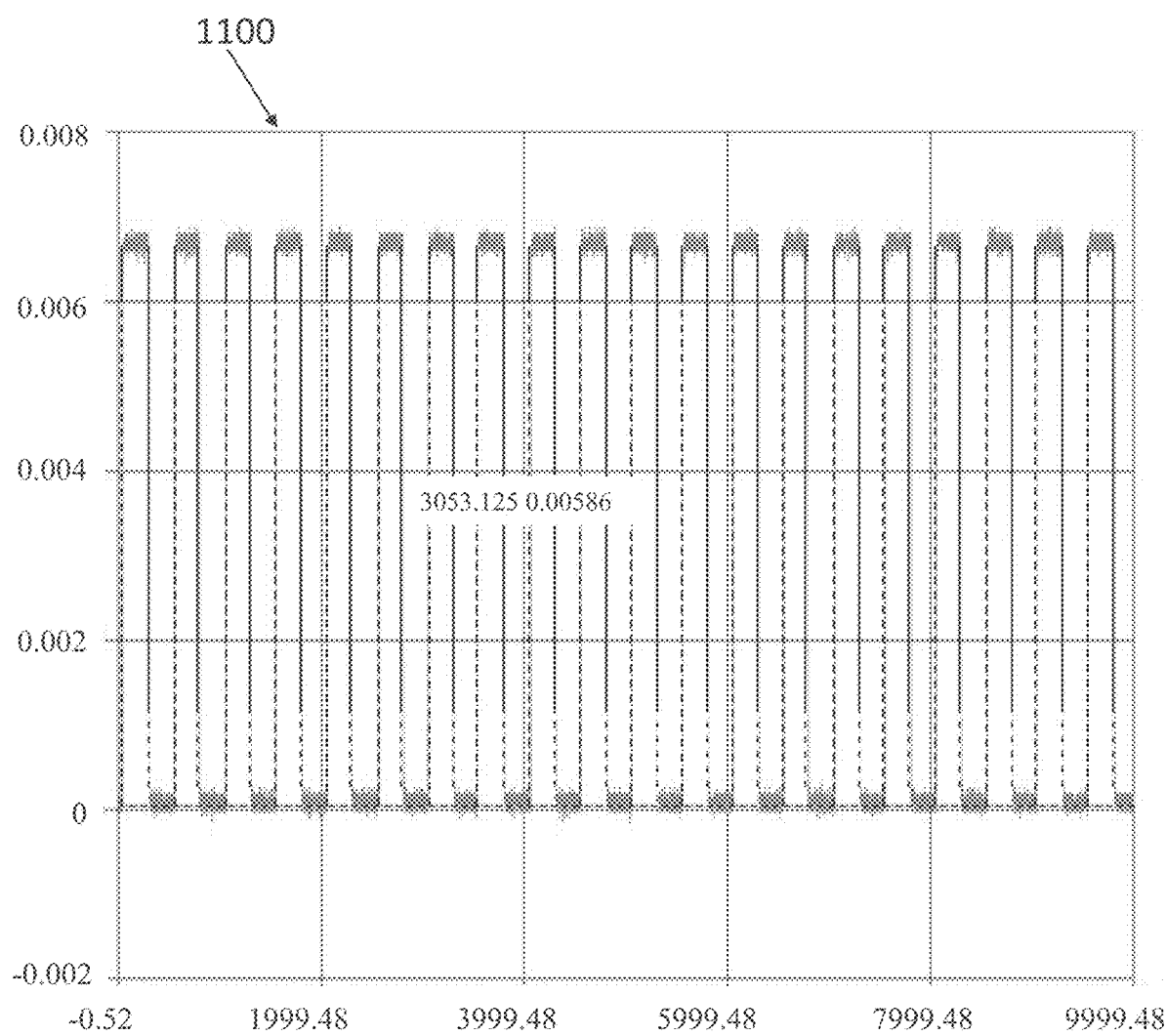
FIG. 11 is graph of an example of an ERG showing photo response at 10 seconds, 2 Hz (4 reversals/second), start points 85%-15%, using the subject system and method.

FIG. 11 is a graph of an example of a ERG showing photo response at 10 seconds, 2 Hz (4 reversals/second), start points 85%-15%, using the subject system and method, shown generally at 1100. Referring to FIGS. 10 and 11, the graphs show photosensitive device responses. Method: Series 1; Series 2 and 3, signify trigger points, or where a checkerboard pattern begins in the stimulus; and Series 4.

Figure 12:
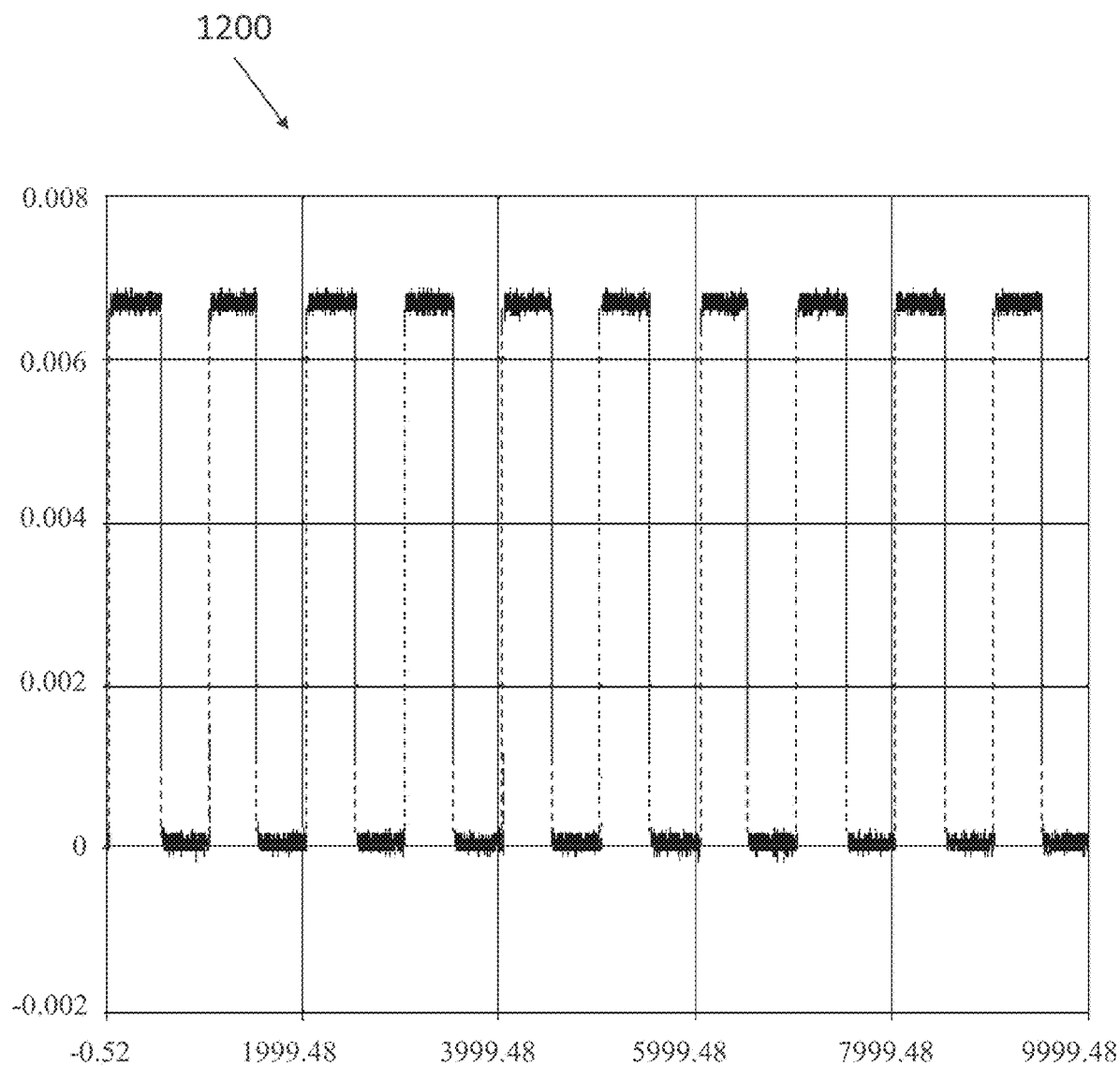
FIG. 12 is graph of an example of a VEP showing photo response at 10 seconds, 1 Hz (2 reversals/second), start points 90%-10% (standard percentages for measuring pixel response time) using the subject system and method.

FIG. 12 is a graph of an example of a VEP showing photo response at 10 seconds, 1 Hz (2 reversals/second), start points 90%-10% (standard percentages for measuring pixel response time) using the subject system and method, shown generally at 1200

Figure 13:
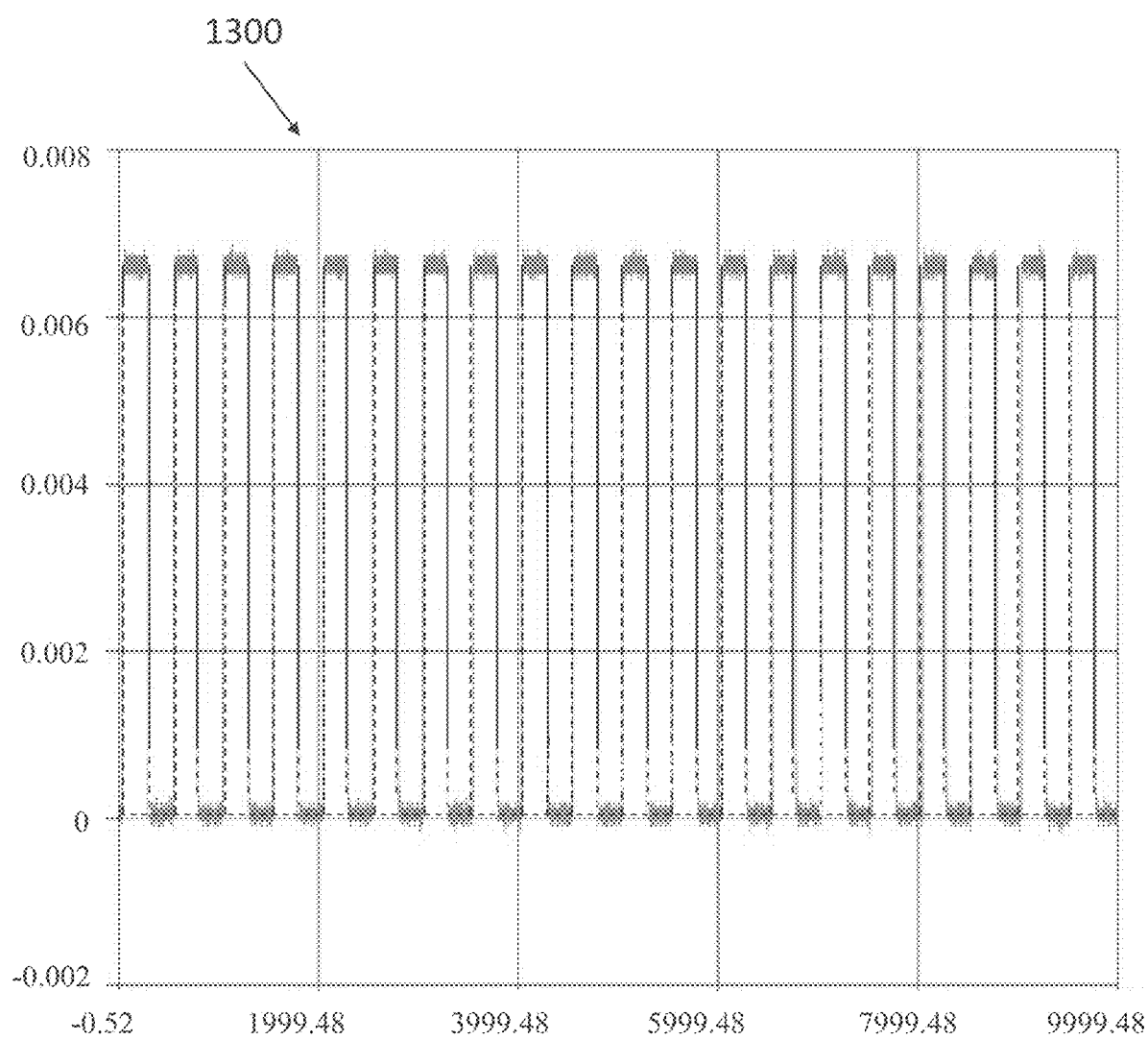
FIG. 13 is graph of an example of an ERG showing photo response at 10 seconds, 2 Hz (4 reversals/second), start points 90%-10% (standard percentages for measuring pixel response time) using the subject system and method.

FIG. 13 is graph of an example of an ERG showing photo response at 10 seconds, 2 Hz (4 reversals/second), start points 90%-10% (standard percentages for measuring pixel response time) using the subject system and method.

Referring to FIGS. 12 and 13, the graphs show photosensitive device responses. Method: Series 1; Series 2 and 3, signify trigger points, or where a checkerboard pattern begins in the stimulus; and Series 4.

The following example is presented to provide a more complete understanding of the invention. The specific techniques, conditions, materials, proportions and reported data set forth to illustrate the principles and practice of the invention are exemplary and should not be construed as limiting the scope of the invention.

EXAMPLE

Research Design: Researchers used a repeated measures design. This design allowed researchers to use a small sample of participants (n=10) for making statistical inference regarding the reliability of the subject system against existing equipment (i.e., Diopsys VEP device). In addition, this design allowed researchers to quickly train participants to complete those tasks required for data collection. Finally, this method allowed researchers to monitor the variance in participants' measures to generate a diagnosis of vision type using a mean measure as opposed to single measure.

Patient Selection: Five patients ("participants") with normal vision were selected, with best corrected visual acuity of 20/25 or better. Each subject had no history of any eye disease and a normal eye examination. Their ages ranged from 26 to 76, with a mean of 40.6 years. Five additional patients were selected who had optic atrophy. Their diagnosis was either optic atrophy—secondary to glaucoma or primary optic atrophy. Their diagnosis was confirmed by OCT, fundus photography, and eye examination.

Procedure: Patients were tested with Diopsys Nova VEP/TR and with the subject system and method. For the purpose of this study, one eye per subject was tested. A 32×32 checkerboard was presented with both devices to produce a visual angle of 30 minutes/check. Gold cup EEG electrodes were applied, using Ten20 (TN) conductive paste (Weaver & Co., Aurora, Colo. USA) after cleaning the scalp with N uprep (TN) cleanser (Weaver & Co., Aurora, Colo. USA). The images were reversed using light inversion modification. The electrodes were placed 2 cm above the brow in the center of the forehead, 2 cm above the inion at the back of the head, and equidistant from the other electrodes at the top of the head. The electrode impedance was measured to be below 5 KΩ with a Prep-Check EIM105 (TN) 30 Hz electrode impedance meter (General Devices, Richfield, N.J. USA). The right eye was patched and the left eye was tested for 10 seconds. This procedure was repeated for a total of three times for each device. The setting for the Diopsys Nova VEP/TR was OS, 10 seconds, checkerboard pattern 32×32, measuring an angle of 30 minutes/check. The contrast was set to 85% with a mean luminance of 66.25 cd/meter$^2$. The pattern reversal speed was set to 1 Hz, or 2 reversals/second. The electrode impedance was checked before testing with our device. The device was set to OS, 10 seconds, checkerboard pattern measuring 30 minutes/check, set to 85% contrast with a mean luminance of 46.9 cd/meter$^2$. The pattern reversal speed was set to 1 Hz, or 2 reversals/second. Analysis design: Researchers used a three-phase analysis design. In the first phase, researchers used descriptive analysis on participants' repeated measures to generate mean scores to diagnose participants' vision type. Participants with mean scores less than 100 milliseconds were diagnosed as normal vision type and recorded as 0. In contrast, participants with mean scores greater than 100 milliseconds were diagnosed as abnormal vision type and recorded as 1. In the second phase, researchers used a one-sample t-test to determine the likelihood participants equally represented both the normal and abnormal vision type populations. Specifically, the mean score for all participants was compared against the industry measure of 100 milliseconds. In the third phase, researchers used a 0-square test of independence on participants' recorded values to determine whether a significant difference exists between either the subject system or the Diopsys device in the diagnosis of vision type and participants known vision type.

Results

Phase 1 Analysis

All participants completed three measures on both machine types. The mean measure for the three tests ranged between 102.78 and 107.36. The standard deviation across the three tests ranged between 18.63 and 22.61. Finally, the mean measure across all vision types equaled 105.39 with a standard deviation of 19.60.

Phase 2 Analysis

The participants' mean measure equaled 105.39 (SD=19.60; see Table 1). Results of the one sample t-test indicates no difference between the participants mean measure and the industry cutoff measure of 100 milliseconds, t(19)=1.23, p=0.234.

Results from both the Phase 1 Analysis and Phase 2 Analysis supports two assumptions. First, the distribution for the measured data for all participants revealed consistent returns across all three tests. Therefore, consistency of data to diagnose participants' vision type regardless of machine type can be assumed. Second, the participants' mean measure and the 100 millisecond standard as cutoff point for differentiating between normal and abnormal vision were equal, statistically. The purpose of phase one and phase two analysis is to demonstrate that the populations of normal and abnormal are clinically and statistically different. This supports an assumption of equal number of participants for the two data sets (i.e. normal vision and abnormal vision participants) used in the ▢-square test associated with the Phase 3 analysis.

Phase 3 Analysis

Differences in the effectiveness of the two machines for total time in completing diagnosis for vision type were found. The cross distribution (see Table 2) for both machines for abnormals and normals revealed differences in the accuracy of diagnosis between the Diopsys device and the subject system. For example, the Diopsys device incorrectly diagnosed 4 of the normal vision patients as abnormal. In addition, the Diopsys device correctly diagnosed all 5 of the abnormal vision patients as abnormal. In contrast, the subject system accurately diagnosed all 5 of the normal patients as normal. In addition, the subject system accurately diagnosed 3 of the abnormal vision patients as abnormal. The remaining two abnormal vision participants in the group were diagnosed using the subject system as "normal", but a closer look at the abnormal patient population shows that those subjects had normal visual acuities (20/20 and 20/25). The subject system accurately defines these two subjects as having normal vision, despite the appearance of the optic nerve. This is consistent with clinical findings, i.e., patients with glaucomatous optic atrophy often have excellent central visual acuity until end-stage disease.

TABLE 1

Acuities and Refractive Error with P100 Results for All Ten Subjects

| Subject | OS SPH | OS CYL | OS AXIS | OS ACUITY | First Test P100 (ms) | Second Test P100 (ms) | Third Test P100 (ms) | Mean Test P100 (ms) |
|---|---|---|---|---|---|---|---|---|
| DATA: NORMAL PATIENTS ||||||||| 
| Diopsys |||||||||
| Subject 1 | −2.25 | −0.75 | 150 | 20/25 | 91.8 | 123 | 148.4 | 121.1 |
| Subject 2 | −3.50 | −0.50 | 95 | 20/20 | 118.2 | 119.1 | 118.2 | 118.5 |
| Subject 3 | 0.00 | 0.00 | 0 | 20/20 | 98.6 | 98.6 | 92.8 | 96.7 |
| Subject 4 | −4.00 | −0.75 | 80 | 20/25 | 107.4 | 118.2 | 97.6 | 107.7 |
| Subject 5 | −3.25 | −0.50 | 175 | 20/20 | 112.3 | 112.3 | 110.3 | 111.6 |
| Siwoff |||||||||
| Subject 1 | −2.25 | −0.75 | 150 | 20/25 | 74.0 | 79.2 | 75.0 | 76.0 |
| Subject 2 | −3.50 | −0.50 | 95 | 20/20 | 88.5 | 89.6 | 101.0 | 93.1 |
| Subject 3 | 0.00 | 0.00 | 0 | 20/20 | 82.8 | 79.7 | 72.4 | 78.3 |
| Subject 4 | −4.00 | −0.75 | 80 | 20/25 | 83.3 | 92.7 | 100.5 | 92.2 |
| Subject 5 | −3.25 | −0.50 | 175 | 20/20 | 96.4 | 99.5 | 97.4 | 97.7 |
| DATA: ABNORMAL PATIENTS ||||||||| 
| Diopsys |||||||||
| Subject 6 | −4.25 | −0.75 | 85 | 20/120 | 90.8 | 109.4 | 120.1 | 106.8 |
| Subject 7 | −0.50 | 0.00 | 0 | 20/40 | 132.8 | 121.1 | 121.1 | 125.0 |
| Subject 8 | −1.50 | −1.50 | 135 | 20/50 | 169.9 | 153.3 | 140.6 | 154.6 |
| Subject 9 | −7.25 | −0.75 | 100 | 20/20 | 108.4 | 105.5 | 123 | 112.3 |
| Subject 10 | 0.00 | 0.00 | 0 | 20/25 | 103.5 | 101.6 | 106.4 | 103.8 |
| Siwoff |||||||||
| Subject 6 | −4.25 | −0.75 | 85 | 20/120 | 125.5 | 123.4 | 121.9 | 123.6 |
| Subject 7 | −0.50 | 0.00 | 0 | 20/40 | 83.3 | 93.3 | 78.6 | 85.1 |
| Subject 8 | −1.50 | −1.50 | 135 | 20/50 | 112.5 | 120.8 | 141.1 | 124.8 |
| Subject 9 | −7.25 | −0.75 | 100 | 20/20 | 101.0 | 103.1 | 101.0 | 101.7 |
| Subject 10 | 0.00 | 0.00 | 0 | 20/25 | 74.5 | 77.6 | 79.7 | 77.3 |

TABLE 2

Raw Measures Generated For 10 Participants
Generated From The Subject System And Diopsys Device

| Participant | Vision type | Machine type | Measure Test 1 | Test 2 | Test 3 | Mean |
|---|---|---|---|---|---|---|
| 1 | Normal | Diopsys | 91.8 | 123.0 | 148.4 | 121.07 |
| 1 | Normal | Subject System | 74.0 | 79.2 | 75.0 | 76.07 |
| 2 | Normal | Diopsys | 118.2 | 119.1 | 118.2 | 118.50 |
| 2 | Normal | Subject System | 88.5 | 89.6 | 101.0 | 93.03 |
| 3 | Normal | Diopsys | 98.6 | 98.6 | 92.8 | 96.67 |
| 3 | Normal | Subject System | 82.8 | 79.7 | 72.4 | 78.30 |
| 4 | Normal | Diopsys | 107.4 | 118.2 | 97.6 | 107.73 |
| 4 | Normal | Subject System | 83.3 | 92.7 | 100.5 | 92.17 |
| 5 | Normal | Diopsys | 112.3 | 112.3 | 110.3 | 111.63 |
| 5 | Normal | Subject System | 96.4 | 99.5 | 97.4 | 97.77 |
| 6 | Abnormal | Diopsys | 90.8 | 109.4 | 120.1 | 106.77 |
| 6 | Abnormal | Subject System | 125.5 | 123.4 | 121.9 | 123.60 |
| 7 | Abnormal | Diopsys | 132.8 | 121.1 | 121.1 | 125.00 |
| 7 | Abnormal | Subject System | 83.3 | 93.3 | 78.6 | 85.07 |
| 8 | Abnormal | Diopsys | 169.9 | 153.3 | 140.6 | 154.60 |
| 8 | Abnormal | Subject System | 112.5 | 120.8 | 141.1 | 124.80 |
| 9 | Abnormal | Diopsys | 108.4 | 105.5 | 123.0 | 112.30 |
| 9 | Abnormal | Subject System | 101.0 | 103.1 | 101.0 | 101.70 |
| 10 | Abnormal | Diopsys | 103.5 | 101.6 | 106.4 | 103.83 |
| 10 | Abnormal | Subject System | 74.5 | 77.6 | 79.7 | 77.27 |
| Mean (SD) | | | 102.78 (22.61) | 106.05 (18.63) | 107.36 (22.07) | 105.39 (19.60) |

Two chi-square tests of independence were conducted to test the hypothesis that Diagnosed vision type and Known vision type were independent across the two machine types. Once again, results from the two tests revealed differences in the effectiveness of the two machines. The relationship between Diagnosed vision type and Known vision type was not significant, $\chi^2(1, n=10)=1.11$, $p>0.05$, for the Diopsys device. This indicates that the Diopsys device failed to effectively differentiate between normal and abnormal vision patients. In contrast, the relationship between diagnosed vision type and known vision type was significant, $\chi^2(1, n=10)=4.29$, $p<0.05$ for the subject system. This indicates that the subject system effectively differentiated between normal and abnormal vision patients.

TABLE 3

Cross Distribution For Machine Type By Vision Type
For The Diagnosis Of Vision Against Known Vision Type

| Machine type | Diagnosis | Known vision type Normal | Abnormal | Total |
|---|---|---|---|---|
| Diopsys | Normal | 1 | 4 | 5 |
| | Abnormal | 0 | 5 | 5 |
| | Sub-total | 1 | 9 | 10 |
| Subject System | Normal | 5 | 0 | 5 |
| | Abnormal | 2 | 3 | 5 |
| | Sub-total | 7 | 3 | 10 |
| Total | | 8 | 12 | 20 |

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A system for measuring electrical activity of a nervous system evoked from visual stimuli presented to an eye of a subject comprising:
   a. an electronic visual display device, for displaying visual stimuli to the subject;
   b. a photosensor for sensing display of the visual stimuli to the subject by the electronic visual display device;
   c. at least one electrode for receiving electrical signals resulting from the subject in response to the visual stimuli;
   d. an analogue to digital converter that converts the electrical signals received from the subject to digital data;
   e. a digital data storage medium for recording the digital data;
   f. a central processing of a computer unit (CPU) with programming to cause the electronic visual display device to display the visual stimuli as a series of at least two images on a timing sequence; and
   g. a synchronizer, which synchronizes each of at least two consecutive images of the visual stimuli from the electronic visual display device with the electrical signal received by the at least one electrode, said synchronizer synchronizing the electrical signals resulting from the subject in response to the visual stimuli with data from the photosensor corresponding to a beginning of a timing cycle for display of said at least two consecutive images;
   wherein the system further comprises programming to cause the CPU to calculate signal averaged digital waveforms based on an average of the electrical signals received from the at least two consecutive images of the visual stimuli.

2. A system as in claim 1, wherein the photosensor is a photodiode.

3. A system as in claim 1, wherein the CPU executes instructions to control display of the at least two images of visual stimuli and the synchronizer operates to synchronize the electrical signals received from the at least one electrode with display of the visual stimuli each of the at least two images presented by the electronic visual display device by adjusting timing of instructions sent to control the electronic visual display device with an input lag, a display lag, or a combination thereof.

4. A system as in claim 1, wherein synchronization is based upon a computer clock directly or indirectly in communication with an atomic clock.

5. A system as in claim 1, wherein the system permits the visual stimuli to be displayed as a series of at least 2 images and the system has programming to instruct the electronic visual display device to display the visual stimuli corresponding to at least one display rate in the range of from 250 m-sec to 500 m-sec per image.

6. A system as in claim 1, wherein the system permits the visual stimuli to be displayed as a series of at least 10 images and the system has programming to instruct the electronic visual display device to display the visual stimuli corresponding to at least one display rate in the range of from 250 m-sec to 500 m-sec per image.

7. A system as in claim 1, wherein said visual stimuli comprises light and said CPU has programming to cause at least two reversals of the visual stimuli.

8. A system as in any of claim 1, wherein said visual stimuli comprises an image of a pattern, design, or object, and said CPU has programming to cause at least 4 reversals of the visual stimuli.

9. A system as in claim 7, wherein said visual stimuli comprises a sequence selected from the group consisting of orientation modification, light modification, alternating images, or a combination thereof.

10. A system as in claim 7, wherein the system permits the visual stimuli to be displayed as a series of at least 2 images and the CPU has programming to instruct the electronic visual display device to display the visual stimuli corresponding to at least one display rate in the range of from 250 msec to 500 msec per image.

11. A system as in claim 7, wherein the system permits the visual stimuli to be displayed as a series of at least 10 images, and the CPU has programming to instruct the electronic visual display device to display the visual stimuli corresponding to at least one display rate in the range of from 250 msec to 500 msec per image.

12. A method for measuring electrical activity of a nervous system evoked from visual stimuli displayed to an eye of a subject, comprising the steps of:
   a. visually displaying visual stimuli to the subject as a series of at least two images with a visual display device according to a timing sequence;
   b. detecting electrical signals from the subject evoked in response to the visual stimuli;
   c. detecting the initial time when each of at least two consecutive images of the visual stimuli is displayed by the video display device, wherein timing for display of the at least two consecutive images is determined by sensing display of light from the visual display device using a photosensor;
   d. synchronizing, with a synchronizer, the electrical signals resulting from the subject in response to the visual stimuli with data from the photosensor corresponding to the initial time and timing each of said at least two consecutive images is displayed to the subject;
   e. converting the electrical signals to digital data for the at least two consecutive images; and
   f. signal averaging the digital data from said at least two consecutive images to provide a signal averaged data for the visual stimuli as a function of time.

13. A method as in claim 12, wherein the photosensor is a photodiode.

14. A method as claim 12, wherein synchronizing the ERG data with the visual stimuli is based on timing of actuation of a switch or upon timing of operation of programming instructions for controlling the video display device, and wherein timing for actuation of said switch or timing of operation of said programming instructions is adjusted by input lag, display lag, or a combination thereof.

15. A method as in claim 12, wherein synchronizing is conducted based on a clock synchronized with an atomic clock.

16. A method as in claim 12, wherein said at least two images of the visual stimuli comprises at least two reversals.

17. A method as in claim 12, wherein said visual stimuli comprises a sequence selected from the group consisting of orientation modification, light modification, alternating images, and combinations thereof.

18. A method as in claim 16, wherein the electrical signals are detected using electrodes placed on or in vicinity to the eye of the subject.

19. A method as in claim 18, wherein the visual stimuli is displayed as a series of at least 10 images and the visual display device is controlled by a CPU with programming to display the visual stimuli corresponding to at least one display rate in the range of from about 125 msec to about 250 msec per image.

20. A method as in claim 17, wherein the electrical signals are detected using electrodes placed on a scalp of the subject.

21. A method as in claim 20, wherein the visual stimuli is displayed as a series of at least 10 images and the visual display device is controlled by a CPU with programming to display the visual stimuli corresponding to at least one display rate in the range of from about 250 msec to about 500 msec per image.

22. A non-transitory computer storage readable medium for a vision examination system, comprising computer-useable instructions that, when used by one or more computing devices, cause the one or more computing devices to:
   a. instruct a visual display device to display visual stimuli to a subject as a series of at least two images according to a timing sequence;
   b. receive electrical signals from a subject to whom said visual stimuli is displayed that evoked as a result of visual exposure to the visual stimuli;
   c. receive data from a photosensor for detecting an initial time when each of at least two consecutive images of the visual stimuli is displayed by the video display device;
   d. synchronize the electrical signals evoked as a result of visual exposure to the visual stimuli with the initial time each of said at least two consecutive images is displayed to the subject;
   e. convert the electrical signals to digital data for said at least two consecutive images; and
   f. signal average the digital data from said at least two consecutive images to provide a signal averaged data for the visual stimuli as a function of time.

23. A non-transitory computer storage readable medium as in claim 22, further comprising instructions to signal average the digital data for at least two, preferably at least 10, consecutive images of the visual stimuli.

24. A system for measuring electrical activity of a nervous system evoked from visual stimuli presented to an eye of a subject, comprising:
   a. an electronic visual display device, for displaying visual stimuli to the subject;
   b. at least one electrode for receiving electrical signals resulting from the subject in response to the visual stimuli;
   c. an analog to digital converter that converts the electrical signals received from the subject to digital data;
   d. a digital data storage medium for recording the digital data;
   e. a central processing unit (CPU) of a computer with programming to cause the electronic visual display device to display the visual stimuli as a series of at least two images on a timing sequence;
   f. a photosensor for sensing for sensing light emitted by the electronic visual display device; and
   g. a synchronizer, which synchronizes each of the at least two images of the visual stimuli from the photosensor corresponding to a beginning of a timing cycle for display of said at least two images;
   wherein the system further comprises programming to cause the CPU to calculate signal averaged digital waveforms based on an average of the electrical signals received from said at least two images of the visual stimuli.

25. A system as in claim 24, wherein said photosensor is a photodiode for sensing display of the at least two images of the visual stimuli by the electronic visual display device.

26. A system as in claim 25, wherein said photodiode senses light emitted by the electronic visual display device, and said synchronizer synchronizes the electrical signals received from the at least one electrode with data from said photodiode corresponding to the beginning of the timing cycle for display of said at least two images.

27. A system as in claim 24, wherein the CPU with programming (i) retrieves status of the electrical signals and calculates a curCount and tick count as a function of time, wherein the tick count=Time/Time Scale; (ii) at a max tick count stores the tick count and curCount into a Data[x][y] array, where x=tick count and y=number of samples per checkerboard; (iii) queries an atomic clock for exact timing; (iv) determines an average array based on (Data[x][y] arrays)/(total tick counts); and (v) presents the average array on the electronic visual display with the Time Scale.

* * * * *